(12) United States Patent
Almutairi et al.

(10) Patent No.: US 9,409,322 B2
(45) Date of Patent: Aug. 9, 2016

(54) SINGLE STEP POLYMERIZATION OF COVALENTLY BOUND MULTILAYER MATRICES

(71) Applicant: The Regents of the University of California, Oakland, CA (US)

(72) Inventors: Adah Almutairi, La Jolla, CA (US); Yogesh Ner, McAllen, TX (US); Jerome Karpiak, San Diego, CA (US); Jose Morachis, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 466 days.

(21) Appl. No.: 13/794,546

(22) Filed: Mar. 11, 2013

(65) Prior Publication Data
US 2013/0234372 A1    Sep. 12, 2013

Related U.S. Application Data

(60) Provisional application No. 61/609,300, filed on Mar. 10, 2012.

(51) Int. Cl.
| | |
|---|---|
| *B29C 39/12* | (2006.01) |
| *A61L 27/52* | (2006.01) |
| *A61L 27/16* | (2006.01) |
| *A61L 27/18* | (2006.01) |
| *A61L 27/26* | (2006.01) |
| *A61L 27/38* | (2006.01) |
| *A61L 27/50* | (2006.01) |
| *A61L 27/54* | (2006.01) |
| *A61L 27/56* | (2006.01) |
| *B29C 67/00* | (2006.01) |

(52) U.S. Cl.
CPC .............. *B29C 39/123* (2013.01); *A61L 27/16* (2013.01); *A61L 27/18* (2013.01); *A61L 27/26* (2013.01); *A61L 27/38* (2013.01); *A61L 27/50* (2013.01); *A61L 27/52* (2013.01); *A61L 27/54* (2013.01); *A61L 27/56* (2013.01); *A61L 2300/252* (2013.01); *B29C 67/0066* (2013.01); *B29C 67/0085* (2013.01); *B29C 67/0092* (2013.01)

(58) Field of Classification Search
CPC ............ B29C 67/0066; B29C 67/0085; B29C 67/0092; B29C 39/123; A61L 27/26; A61L 27/16; A61L 27/18; A61L 2300/252; A61L 27/38; A61L 27/50; A61L 27/52; A61L 27/54; A61L 27/56; C08L 71/02; C08L 33/04; C08L 33/08
USPC .................................................. 264/308, 496
See application file for complete search history.

(56) References Cited

U.S. PATENT DOCUMENTS

2011/0184455 A1* 7/2011 Keeley et al. ................. 606/200

OTHER PUBLICATIONS

Nguyen et al. (K.T. Nguyen and J.L. West, "Photopolymerizable hydrogels for tissue engineering applications", Biomaterials 23 (2002) 4307-4314 (accepted Jan. 14, 2002), hereinafter Nguyen).*

*Primary Examiner* — Robert J Grun
(74) *Attorney, Agent, or Firm* — Eleanor Musick; Musick Davis LLP

(57) ABSTRACT

A method is provided for forming complex tissue using density gradient multilayer polymerization (DGMP) to form strong hydrogels with smooth transitions between layers. The multicompartment hydrogel is formed by co-dissolving a polymer precurser with a constituent in multiple solvent fractions to a create prepolymer solutions with different densities, layering the prepolymer solutions on top of each other from high to low solvent density, and irradiating the prepolymer solutions to form a polymer. The hydrogels may be used as biomimetic matrices.

20 Claims, 20 Drawing Sheets

Figure 5: DGMP can be adapted to produce hydrogels of varying shapes. Multicompartment PAM (a) and PEGda (b & c) hydrogels fabricated as outlined in Figure 1a for several geometries. Discrete layers are indicated by alternating flourescein-o-acrylate or rhodamine B.

Large ticks indicate 5 mm.

Figure 6: DGMP can separate protein into discrete compartments. PEGda hydrogels were created via DGMP in which BSA-594 was encapsulated in alternate (a) and adjacent (b) layers. Normalized average intensity plots indicate relative BSA-594 concentrations below images. Bar indicates 500 μm.

Figure 13: $^1$H-NMR confirms acryloyl-PEG-RGDS. $^1$H NMR (500 MHz, D$_2$O) δ 6.42 (dd, J=17.4, 1.1 Hz, 1H), 6.19 (dd, J=17.3, 10.5 Hz, 1H), 5.97 (dd, J=10.6, 1.1 Hz, 1H), 4.40–4.30 (m, 3H), 4.11 (d, J=3.9 Hz, 1H), 4.08 (s, 1H), 3.95 (d, J=3.5 Hz, 1H), 3.88–3.48 (m, 316H), 3.19 (t, J=6.9 Hz, 2H), 2.88 (dd, J=16.9, 5.0 Hz, 1H), 2.79 (dd, J=16.9, 8.0 Hz, 1H), 1.9 (m, 1H), 1.78 (m, 1H), 1.64 (m, 3H).

SINGLE STEP POLYMERIZATION OF COVALENTLY BOUND MULTILAYER MATRICES

RELATED APPLICATIONS INFORMATION

This application claims the benefit of priority under 35 U.S.C. §119(e) of U.S. Provisional Application Ser. No. 61/609,300, filed Mar. 10, 2012, and entitled SINGLE STEP POLYMERIZATION OF COVALENTLY BOUND MULTI-LAYER MATRICES, which is incorporated herein by reference in its entirety as if set forth in full.

GOVERNMENT RIGHTS

This invention was made with government support under Grant No. DMR1006081, awarded by the National Science Foundation. The government has certain rights in the invention.

FIELD OF THE INVENTION

The present invention relates to a method for creating complex tissue. More specifically, the present invention provides a new method known as "density gradient multilayer polymerization (DGMP)", which uses inexpensive reagents to form strong hydrogels with smooth transitions between layers. These novel hydrogels may be used as biomimetic matrices.

BACKGROUND OF THE INVENTION

Tissue engineering has recently focused on biomimetic matrices, usually polymer hydrogels, that include multiple layers with distinct structures and chemical components. (see, P. X. Ma, Adv. Drug Deliv. Rev. 2008, 60, 184; K. Y. Lee, et al., Chem. Rev. 2001, 101, 1869; A. Khademhosseini, et al., Biomaterials 2007, 28, 5087).

Current methods of fabricating such matrices are complex or expensive to implement and often produce mechanical weaknesses between layers. (see, E. S. Place, et al., Nat. Mater. 2009, 8, 457) Thus, an adaptable, facile, and economical multilayer polymer fabrication technique that produces continuous interfaces between layers is needed.

Existing strategies allow for construction of multiphase scaffolds with varying degrees of complexity. Multiphase biopolymer-based hydrogel matrices have been previously fabricated by additive photopatterning, (see, V. A. Liu, et al., Biomed. Microdevices 2002, 4, 257; J. H. Elisseeff, et al., Tissue Eng.g 2007, 13, 405; L. M. Weber, C. Y. Cheung, K. S. Anseth, Cell Transplantation 2008, 16, 1049), laser scanning lithography (see, M. S. Hahn, et al., Adv. Materials 2005, 17, 2939), printing (see, T. Boland, et al., Biotechnology J. 2006, 1, 910), sequential functionalization (see, S. Kizilel, et al., Biomaterials 2006, 27, 1209), and freeze-drying (see, B. A. Harley, et al., J. Biomed. Mater. Res. A 2010, 92, 1078; S. Varghese, et al., J. Mater. Chem. 2010, 20, 345).

Additionally, spatial control of chemical or mechanical gradients has been achieved using gradient makers (see, K. Chatterjee, et al., Biomaterials 2010, 31, 5051), microfluidics (see, S. Cosson, et al., Adv. Funct. Materials 2009, 19, 3411; J. He, et al., Adv. Funct. Materials 2010, 20, 131; M. P. Cuchiara, et al., Biomaterials 2010, 31, 5491), and centrifugation (see, J. L. Roam, et al., Biomaterials 2010, 31, 8642). Another approach is to attach layers after fabrication (see, K. S. Straky, et al., Adv. Materials 2009, 21, 4148; J. P. Gleghorn, et al., J. Biomed. Materials Res.-A 2008, 85, 611).

However, these techniques may not be widely adopted because they require sophisticated instrumentation and/or technical proficiency.

SUMMARY OF THE INVENTION

The inventive method allows for conventional single step polymerization of multi-compartment polymer matrices. The described method is further unique in that the number of compartments is not limited by the procedure. Moreover, structural integrity is not compromised between layers or across gradients due to partial or incomplete interfacial integration. Properties of the resultant multilayer substrate are fully modulated by predetermination of discrete precursors separated by adjacent solvent liquid phase density dissimilarity and settling time of the solvent gradient. Additionally, the method is versatile, simple, requires ordinary adaptable reagents without additional heating or cooling steps, and is fully amenable to complimentary techniques, including competitive methods, to further direct multiscale polymer matrix architecture.

In one aspect of the invention, solutions of the components of each layer, including polymers, are mixed with varying concentrations of a common inert reagent to control density. The solutions are layered so that the difference in density segregates each solution, and then polymerized to form a gel. The structure of each layer can be altered by varying the concentration of polymers, and the discreteness of the transition between layers can be altered by allowing the solutions to diffuse.

This method, termed Density Gradient Multilayer Polymerization (DGMP), exploits phase separations between liquids of varying density to create layers of distinct structure and chemical composition. Briefly, serial concentrations of an inert density modifier, such as sucrose or iodixanol, are co-dissolved with a prepolymer (such as bisacrylamide and acrylamide or biocompatible c(PEGda)), crosslinkers, and ligands, proteins or cells.

Next, these prepolymer solutions are gently layered on top of each other in order of decreasing density. Varying the initial concentrations and types of each of these agents in each layer allows structures and chemical properties to be tailored. Varying the settling time before polymerization ($t_S$) adjusts the smoothness of gradients between layers. Bulk polymerization yields a multicompartment hydrogel. Finally, the density modifier is removed, resulting in multiphase hydrogels that are structurally uninterrupted at interfaces of chemically and mechanically diverse layers.

Density gradient multilayer polymerization allows engineering of multiple properties, either separately or combinatorially, into discrete or gradient phases of a structurally continuous polymer-based scaffold. Non-limiting tunable properties include: covalently bound or encapsulated functional motifs and/or proteins; encapsulated cell type, ratio, density, and organization; minimally manipulated Human Cells, Tissues, and Cellular and Tissue-Based Products (HCT/Ps); matrix swellability, porosity, mechanical stiffness, macro, micro and nano-scale architectures; and responsiveness to cues such as pH, reactive oxygen species, light, enzymatic degradation, temperature.

The polymer based scaffolds/gels can also be formulated in different shapes to further control the release of encapsulated materials. This can be achieved via the gradient, multilayer, or combined systems in a flat gel, 3-dimensional gel, or a rolled gel.

In one aspect of the invention, a polymer precursor with a predetermined property is organized in discrete phases by static density gradient separation. Briefly, multilayer solvents are separately prepared via sequential dilution of a density modifier, such as sugar, salt, or iodixanol (in cases of aqueous precursors). Precursor constituents are dissolved separately, or in combination, in a solvent preparation corresponding to the desired layer, in order of density. Solvents are sequentially added to vessel of desired geometry. After a settling duration, precursors are polymerized to form a multi-compartment polymer matrix.

Due to the tissue like properties, this invention has many applications in tissue engineering. It allows for full control of each layer's content in multilayer gels. Additionally it can function as an inductive/conductive multilayered scaffold to drive differential cellular behavior. It can be used to create patterned features throughout the gel or in patterns to better mimick certain biological tissues or niche scenarios.

It also has potential applications in therapeutic drug release and delivery. Due to the flexibility and multilayer capability, drug release and delivery can be modulated and controlled. Drugs can be released through controlled diffusion or actively using stimuli responsive polymers within separated compartments.

There is also potential to apply this technology to drug discovery. For example, it can be used to model diseases using human cells to facilitate investigation of migration, polarization, differentiation, and intercellular communication, among other phenomena, in a more in-vivo like setting.

Outside of life sciences, potential commercial applications include multilayered processed food items or the preservation of foods with coatings in the food industry.

DETAILED DESCRIPTION

DGMP exploits phase separations between liquids of varying density to create layers of distinct structures and chemical compositions. Briefly, serial concentrations of an inert density modifier, such as sucrose or iodixanol, are co-dissolved with prepolymer (such as bisacrylamide and acrylamide or biocompatible c(PEGda)), crosslinkers, and ligands or proteins (FIG. 1a and FIG. 1b). Next, these prepolymer solutions are gently layered on top of each other in order of decreasing density. Varying the initial concentrations and types of each of these agents in each layer allows structures and chemical properties to be tailored. Varying the settling time before polymerization ($t_S$) adjusts the smoothness of gradients between layers. Bulk polymerization yields a multicompartment hydrogel. Finally, the density modifier is removed, resulting in multiphase hydrogels that are structurally uninterrupted at interfaces of chemically and mechanically diverse layers.

Reageants are chosen for their suitability for this application. Sucrose is a highly soluble density modifier with a linear relationship between concentration and density (FIG. 1a). Iodixanol, the main ingredient of Optiprep, is a nonionic, iso-osmotic density modifier currently used in viable cell purification (see, G. M. Graziani-Bowering, et al., J. Immunol. Methods 1997, 207, 157; G. J. Brewer, et al., Nat. Protoc. 2007, 2, 1490). Polyethylene glycol and polyacrylamide (PAM)-based hydrogels are well-suited for cell culture applications because they are biologically inert, so they are resistant to non-specific protein adsorption and cell adhesion (see, J. Tang, et al., Biomaterials. 2010, 31, 2470; R. Peng, et al., Biomaterials. 2011, 32, 8048), enabling precise engineering of desired biofunctionality through the covalent addition of ligands such as RGD peptide (see, M. P. Lutolf et al., Nat. Biotechnol. 2005, 23, 47; M. J. Roberts, et al., Adv. Drug Deliv. Rev. 2002, 54, 459; N. A. Peppas, et al., J. Controlled Release 1999, 62, 81; Z. Zhang, et al., Biomaterials. 2010, 31, 7873). With these components, DGMP produces structurally continuous multilayer hydrogels for tissue engineering. Furthermore, the method can be adapted to varying mold shapes, sizes, and materials (FIG. 1b).

Existing techniques, including sequential photopolymerization, may yield networks that are susceptible to delamination under mechanical stress (see, L. M. Weber, et al., Cell Transplantation 2008, 16, 1049; D. Kuckling, et al., Polymer 2008, 49, 1435; P. Calvert, et al., MRS Proceedings, 1997, 489, 153). This mechanical instability is due to discontinuity at layer interfaces. Field emission scanning electron microscopy (FESEM) of architecturally varied PEGda layers reveals enhanced continuity at the interface of hydrogels fabricated by DGMP when compared to sequential polymerization (FIG. 2a compared to FIG. 2b).

Figure 2:
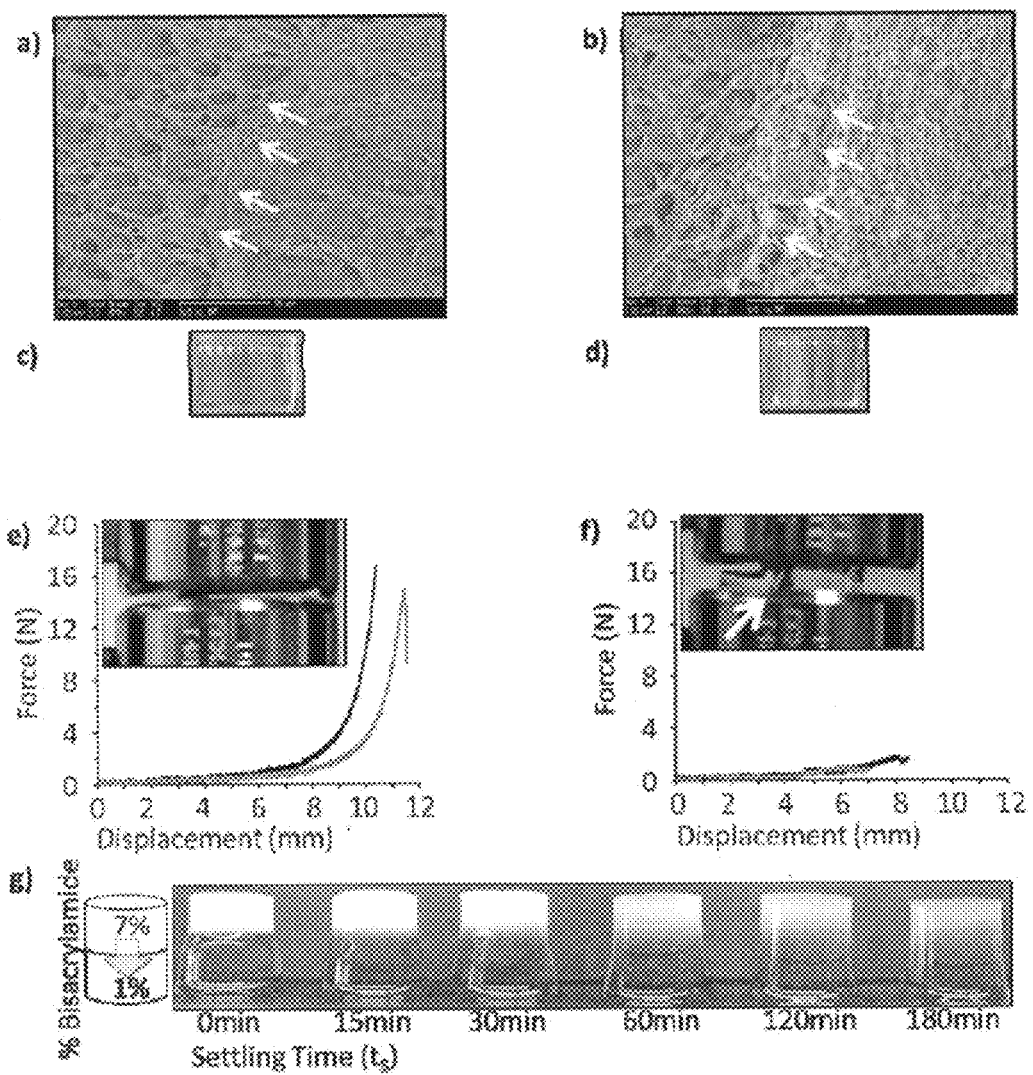
FIG. 2 illustrates DGMP resulting in continuous structures and mechanical stability at interfaces of adjacent compartments in mechanically heterogeneous hydrogels. (a-b) Multicompartment PEGda hydrogels fabricated via sucrose DGMP (a) are microstructurally more continuous at the interface between 10% (w/v, upper left) and 20% (w/v, lower right) prepolymer than sequentially photopolymerized PEGda (b). White arrows highlight interfaces. Bar indicates 50 μm. (c-f) Five-layer PAM (10% w/v, 1% w/w crosslinker) hydrogels approximately 12 mm in diameter prepared by DGMP or sequential photopolymerization. DGMP produces hydrogels (c) that are macrostructurally more continuous than sequentially photopolymerized PAM (d). DGMP produces stronger hydrogels (e) than sequentially photopolymerized PAM (f) as indicated by perpendicular compression to failure and failure mode evaluation Photos are inset in force vs. displacement curves (n=2). Note that DGMP hydrogels bulk ruptured at around 90% strain while sequentially polymerized hydrogels delaminated at around 65% strain as indicated by a white arrow. (g) Increasing tS prior to bulk polymerization modulates structural gradients in 10% (w/v) PAM bilayer hydrogels. As schematically represented (left), bisacrylamide crosslinker diffuses through the density interface to graduate the transition between 7% and 1% crosslinker (w/w monomer). Swelling in water demonstrates the transition from discrete to increasingly continuous mechanical gradients.

This enhanced continuity can also be observed macroscopically in five-layer PAM hydrogels (FIG. 2c compared to FIG. 2d). Moreover, perpendicular compression testing revealed that PAM hydrogels fabricated via DGMP outperform analogous sequentially polymerized hydrogels (FIG. 2e compared to FIG. 2f).

Biomimetic tissue engineering also requires fabrication of not only discrete multicompartment gels but also gradients of varying degrees. To demonstrate the ability of DGMP to produce a variety of gradients, both smooth and sharp, between layers with different structures, we initially created biphasic matrices with 7% and 1% (w/w) PAM precursor using sucrose solutions of distinct densities and varied the settling times. Immediately polymerized hydrogels exhibit discrete compartments, with an abrupt transition, or sharp gradient, with different susceptibilities to swelling (FIG. 2g, left). However, as $t_S$ is incrementally increased prior to bulk polymerization, the lower layer becomes less susceptible to swelling (FIG. 2g, from left to right). This illustrates that increasing settling time increases the graduation in mechanical transition.

To determine whether DGMP allows spatial restriction of biological cues, we designed a simple experiment in which the biological cue would allow cell adhesion; whether the cues were separated would be obvious from whether cells attached. We fabricated tissue culture compatible two-dimensional (2D) substrates with alternating layers of covalently bound aPEG-RGDS labeled with Alexa Fluor 350 (to help visualize patterning) and seeded them with C2C12 myoblasts (FIG. 3a and FIG. 3b).

We developed a small scale manufacturing technique using iodixanol concentration gradients to construct these multilayer disc-shaped PEGda hydrogels specifically for tissue culture with standard well plates (FIG. 1b). Briefly, molds were cut from 0.8 mm silicone sheets sized to fit between glass slides and used to construct seven-layer PEGda substrates via iodixanol DGMP. The tissue-culture discs swelled, were sterilized, and then seeded with C2C12 myoblasts (FIG. 3b).

Figure 3:
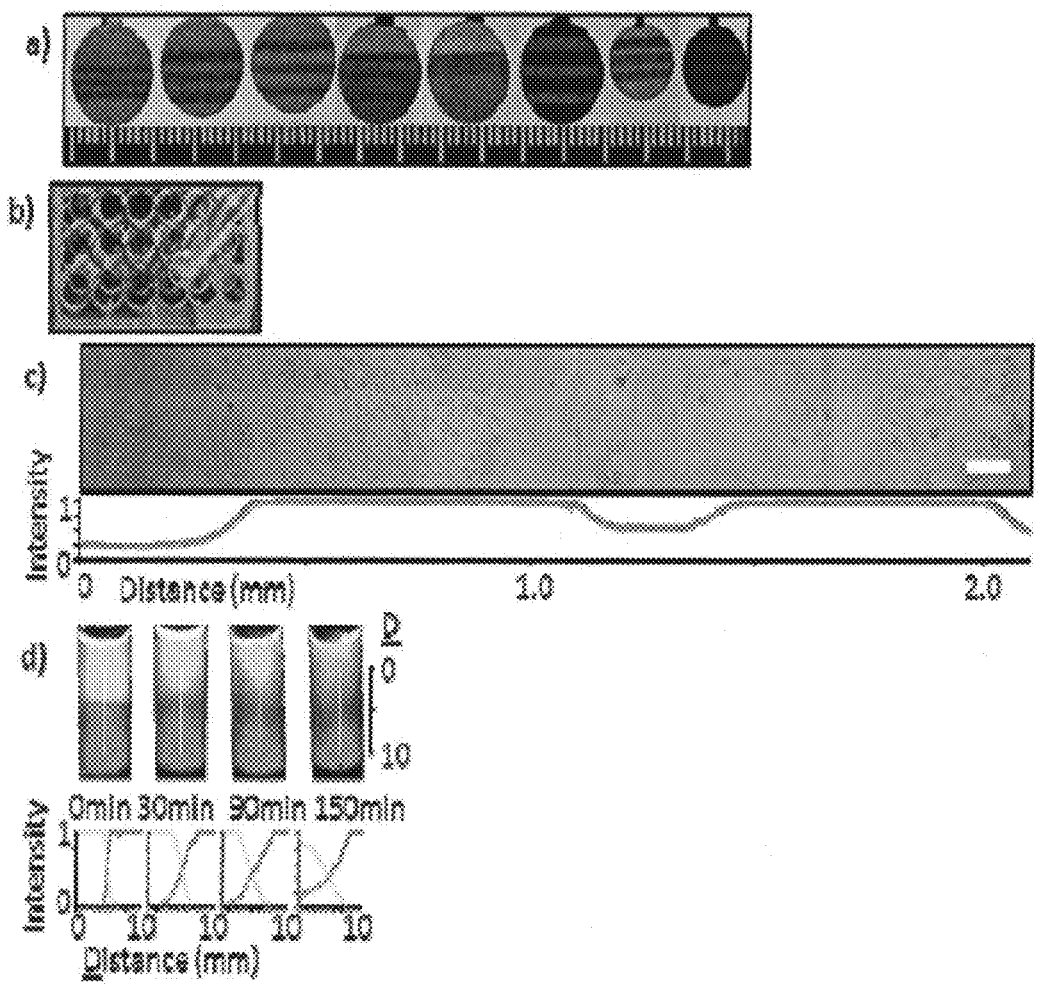
FIG. 3 illustrated DGMP facilitating spatial control of scaffold bioactivity. (a-c) 2D seven-layer PEGda tissue culture substrates prepared as outlined in FIG. 1b for 10 mm (a, left six) and 8 mm (a, right two) hydrogel discs with alternating layers of RGDS-AlexaFluor 350 (8 μM) or methacrylated rhodamine. (b) After swelling, discs are added to tissue culture well plates. (c) Phase contrast image of C2C12 monolayer, color composited with corresponding epifluorescence image. Note that cell spreading is restricted to two regions of PEG-RGDS, additionally indicated by the normalized average fluorescence intensity plot below image. Bar indicates 100 μm. (d) Progressive cross-gradients of Ova-488 (top) and BSA-594 (bottom) encapsulated via DGMP at different tS, as outlined in FIG. 1a, with intensity plots. Scale indicates 10 mm.
Figure 4:
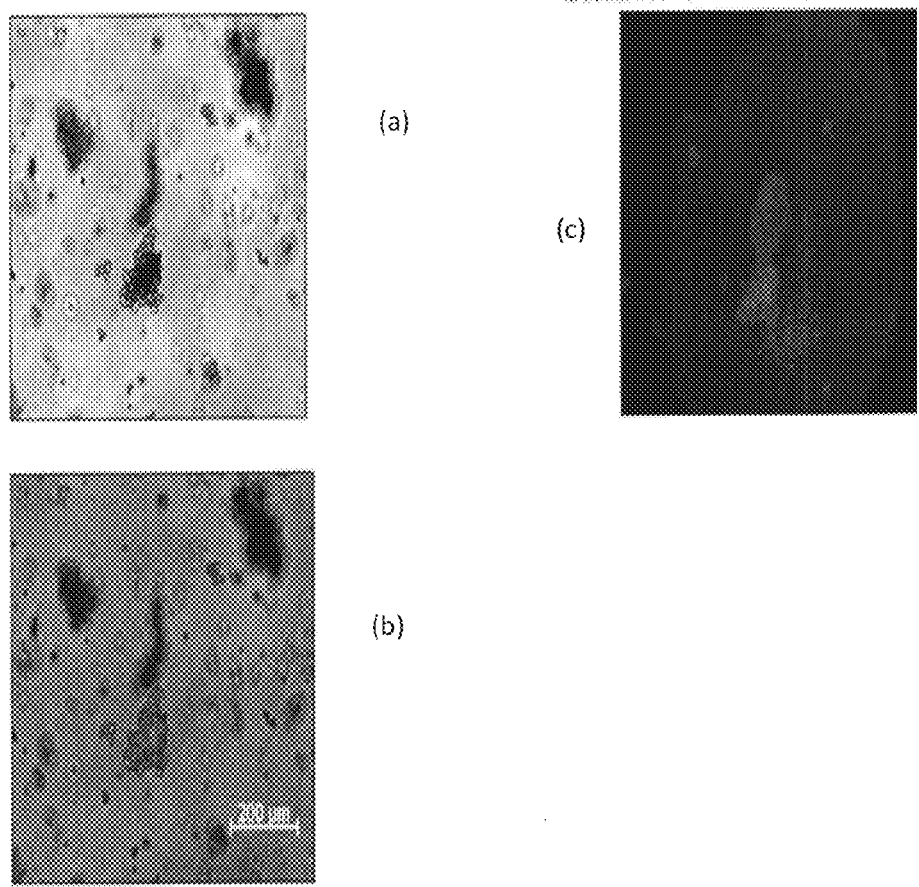
FIG. 4 illustrates photopolymerization in the presence of (35% w/v) iodixanol yields viable cells encapsulate in hydrogels. Day 17 calcein-AM live stain of C2C12 myoblasts encapsulated in PEGda (10% w/v) with bound RGDS 9 mM, photopolymerized in the presence of iodizanol (35% w/v). (a) Brightfield phase contrast. (b) Epifluorescence with FITC filter set. (c) Composite.

It was observed that adhered cells co-localized with covalently grafted RGDS peptide, visualized by alternating substrate fluorescence (FIG. 3c). Furthermore, we were able to photoencapsulate C2C12 myoblasts by photopolymerization of the solutions, containing these cells, to form gels in the presence of 35% (w/v) iodixanol. Briefly, 500,000 cells cm-3 were photoencapsulated in single compartment PEGda hydrogels with 8 mM RGDS and expanding cell colonies were confirmed viable by calcein-AM live stain after two weeks in culture (FIG. 4). These results show that the iodixanol DGMP method allows fast, simple fabrication of hydrogel scaffolds with spatially defined active biological cues.

Figure 5:
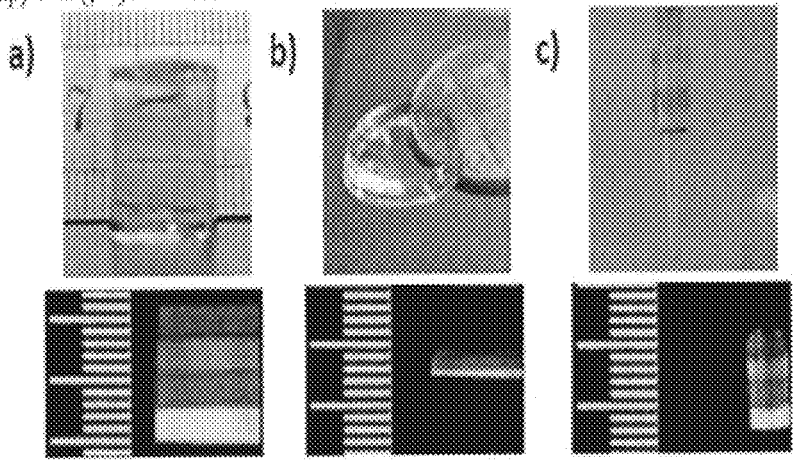
FIG. 5 illustrates that DGMP can be adapted to produce hydrogels of varying shapes. Multicompartment PAM (a) and PEGda (b and c) hydrogels fabricated as outlined in FIG. 1a for several geometries. Discrete layers are indicated by altering fluoresceing-o-acrylate or rhodamine B. Large ticks indicate 5 mm.
Figure 6:
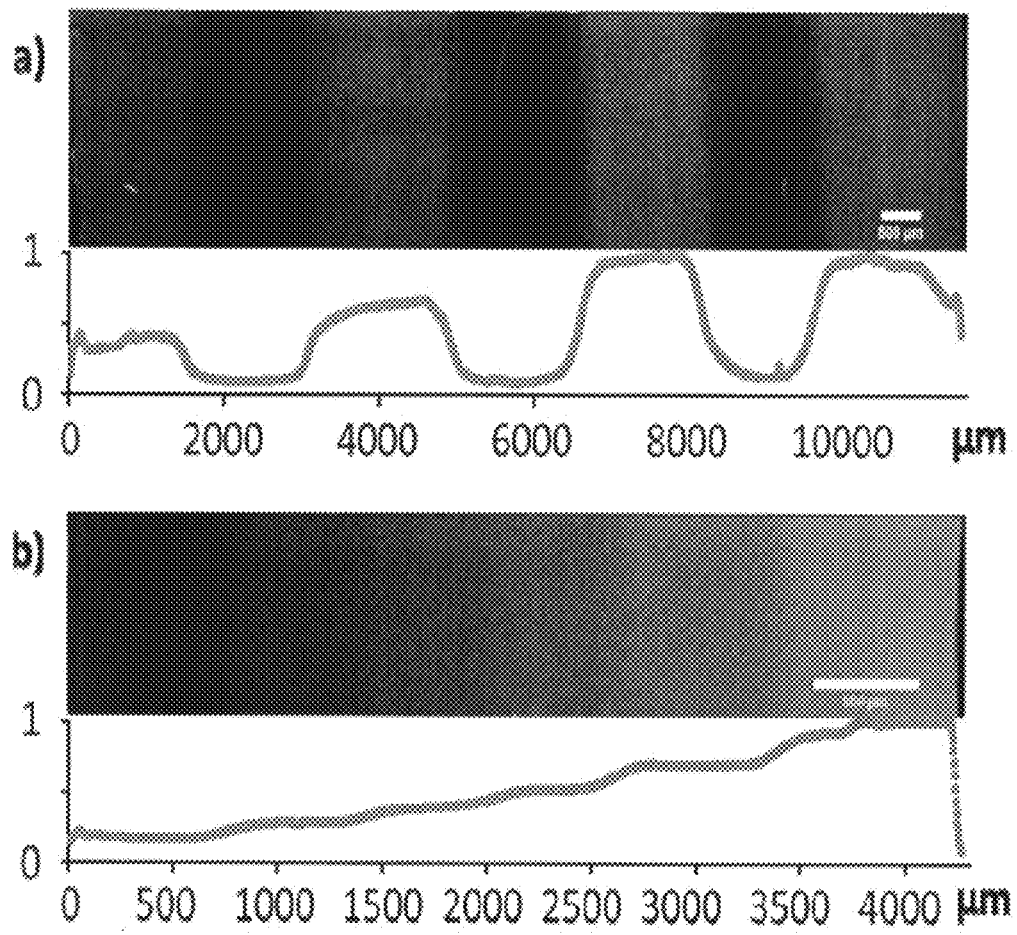
FIG. 6 illustrates that DGMP can separate proteins into discrete compartments. PEGda hydrogels were created via DGMP in which BSA-594 was encapsulated in alternate (a) and adjacent (b) layers. Normalized average intensity plots indicate relative BSA-594 concentrations below images. Bar indicates 500 μm.

To determine whether this method allows spatial control of discretely arranged proteins, we created matrices in which small molecules (fluorescein-o-acrylate or rhodamine B) were bound (FIGS. 5a-5c) or protein was encapsulated (FIG. 3d and FIGS. 6a-6b). Bovine serum albumin (BSA) was encapsulated in alternate layers (FIG. 6a) or in discretely stepped gradients (FIG. 6b). Further, we modulated smooth protein cross-gradients in PEGda hydrogels by increasing $t_S$ after layering sucrose solutions of ovalbumin conjugated to Alexa Fluor 488 (OVA-488, 4 mg mL-; FIG. 3d, top) and BSA conjugated to Alexa Fluor 594 (4 mg mL-; FIG. 3d, bottom). Longer $t_S$ resulted in progressively graduating protein concentration profiles.

Accurately modeling diseases using human cells requires 3D in vitro culture systems that mimic the degree and nature of variation found in vivo: both structural and biochemical, allowing cells to integrate multiple signals from various directions. Not only could such systems be used to create models of layered tissues, but they could also facilitate investigation of migration, polarization, differentiation, and intercellular communication, among other phenomena, in a more in vivo-like setting. Unfortunately, such variation in 3D hydrogel matrices is difficult to generate; current methods to create multilayer or gradient hydrogels involve complex instrumentation that requires technical skill.

Naturally, this has limited the use of such methods to engineering groups, which is unfortunate, as life science labs far outnumber bioengineering labs. The existing techniques that allow construction of multilayer matrices include additive photopatterning (Liu V A, et al., Three-Dimensional Photopatterning of Hydrogels Containing Living Cells. Biomedical Microdevices. 2002; 4(4):257-66), laser scanning lithography (Hahn M S, et al., Three-Dimensional Biochemical and Biomechanical Patterning of Hydrogels for Guiding Cell Behavior. Advanced Materials. 2006; 18(20):2679-84), printing (Boland T, et al., Application of inkjet printing to tissue engineering. Biotechnology Journal. 2006; 1(9):910-7), and sequential functionalization (Kizilel S, et al., Sequential formation of covalently bonded hydrogel multilayers through surface initiated photopolymerization. Biomaterials. 2006; 27(8): 1209-15).

Additional techniques offer spatial control of chemical or mechanical gradients, including gradient makers (Chatterjee K, et al., The effect of 3D hydrogel scaffold modulus on osteoblast differentiation and mineralization revealed by combinatorial screening. Biomaterials. 2010; 31(19):5051-62) and microfluidics (Cosson S, et al., Capturing Complex Protein Gradients on Biomimetic Hydrogels for Cell-Based Assays. Advanced Functional Materials. 2009; 19(21):3411-9.).

An intuitive approach to generate multilayer hydrogels that does not require specialized instruments is serial addition of layers (Kim T K, et al., Experimental Model for Cartilage Tissue Engineering to Regenerate the Zonal Organization of Articular Cartilage. Osteoarthritis and Cartilage. 2003; 11(9): 653-64.), but this creates barriers to diffusion and mechanical weakness at interfaces, and because of repeated UV exposure or cycles of temperature changes, may damage encapsulated cells.

To develop assays for migration, neurite outgrowth, and synaptogenesis, enabling the comparison of iPSC-derived NPCs and neurons generated from Rett syndrome (RTT) patients to those from controls. Because of the adaptability of DGMP, these assays may be modified to suit a variety of neuroscience questions, from the study of responses to specific migratory cues by a particular cell to screening drug candidates for their ability to rescue disease-associated defects in neural organization.

Figure 7:
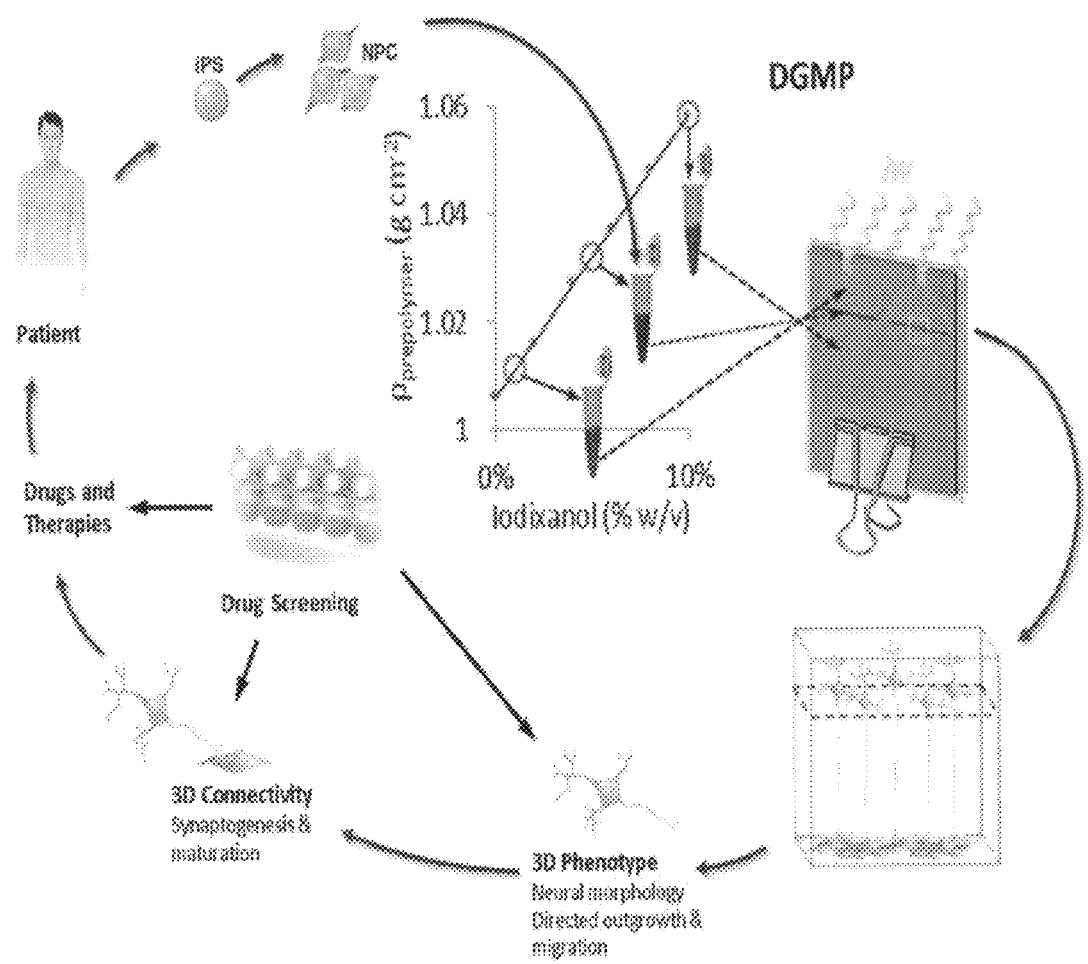
FIG. 7 illustrates the use of DGMP to model neurodevelopmental diseases. Somatic cells from RTT patients and controls are reprogrammed to iPSCs, then directed to become NPCs and encapsulated within a discrete layer of a DGMP hydrogel tissue scaffold. 3D organization enables study of directed neurite outgrowth and migration, and facilitates examination of morphological phenotypes including process branching and spine density/volume/maturation, as well as synapse formation (by immunostaining) Incorporating a somatic target cell layer (e.g., HEK293) allows distinction between autonomous and non-autonomous aspects of the disease. Once a novel disease-related phenotype is identified, the system may be used to screen candidate drugs.
Figure 8:
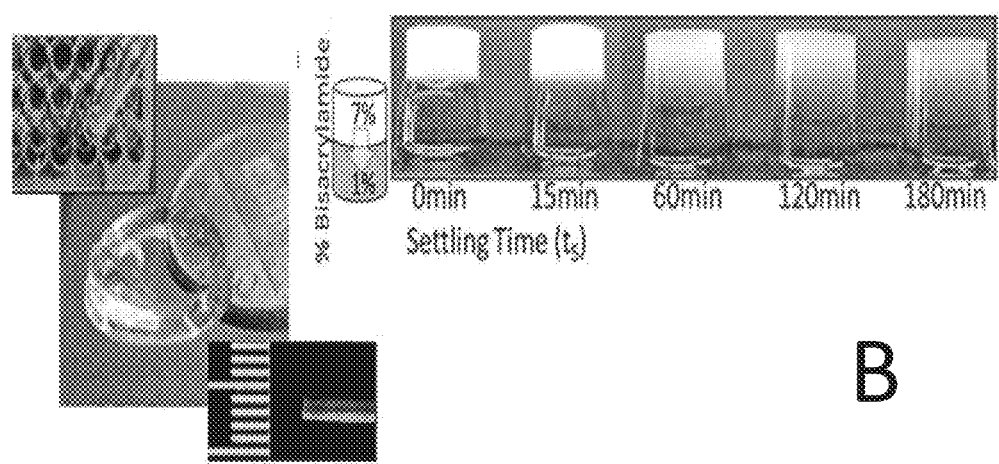
FIG. 8 illustrates that DGMP allows thin layers and gradients. (a) Four-layer tissue culture gels fit into 96 well plates. (b) Continuous crosslinking density gradients by varying settling time.

Current technologies for organizing cells, matrix components, and biochemical cues in 3D are complicated and require expensive equipment. Thus, their use is limited to only a few labs. This narrow application means that other labs must either limit their research questions to those addressable in 2D cell culture or in animals. To study brain disorders, the most appropriate animal models are mice or rats, which can be expensive, and more importantly often yield results that do not correlate with those in human cells. The invention described herein (FIG. 7) bridges the gap between studies in animal models and previous investigations using human iPSC-derived neurons cultured on flat surfaces.

The brain is complex, containing billions of interconnected neurons, forming trillions of individual connections. Its development occurs through the presentation of molecular, structural, and environmental cues presented at precise times in three dimensions. As such, modeling human brain development in vitro presents major challenges. The unavailability of live human neurons for research had until recently represented a major obstacle in the understanding of human brain development. While brain imaging has revealed important macroscale insights, such as increased numbers of neurons in autistic patients (Courchesne E M P, Calhoun M E, Semendeferi K, Ahrens-Barbeau C, Hallet M J, Barnes C C, Pierce K. Neuron number and size in prefrontal cortex of children with autism. JAMA: The Journal of the American Medical Association. 2011; 306(18):2001-10), understanding local circuit development is also important for understanding neurological disease. In addition, while animal models are an important tool, they often do not recapitulate human phenotypes, and have been particularly problematic in the case of human neurodevelopmental diseases such as autism.

Figure 9:
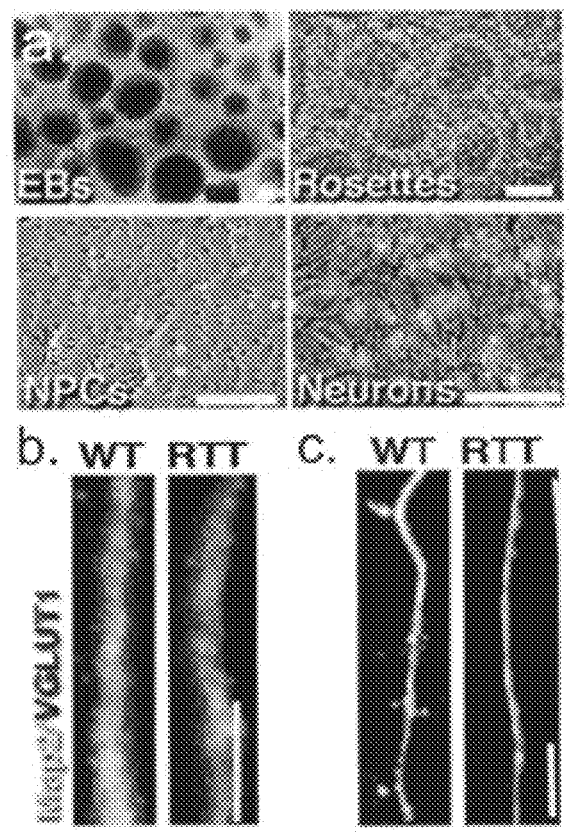
FIG. 9 illustrates characterization of iPSC-derived neurons. (a) Representative images depicting morphological changes during neurogenesis. Bar=100 μm. (b) Compared to WT, RTT neurons displayed impaired connectivity with reduced synapses and (c) and spine density. Bar=5 μm.

The development of induced pluripotent stem cell (iPSC) technology overcame some of these limitations, but the lack of methods to organize neurons in 3D (see Rationale) has limited observable phenotypes to mostly individual characteristics, such as morphology and spontaneous electrical activity. iPSCs have enabled the generation of neurons from patients (FIG. 9a), allowing our recent investigation of RTT pathology, one of the first to use this breakthrough system to study neurodevelopmental disorders (Marchetto M C N, Carromeu C, Acab A, Yu D, Yeo G W, Mu Y, et al. A Model for Neural Development and Treatment of Rett Syndrome Using Human Induced Pluripotent Stem Cells. Cell. 2010; 143(4): 527-39).

Studying RTT, which affects 1:10,000-1:22,000 births, may reveal mechanisms involved in other autism spectrum disorders. RTT is especially amenable to study because its genetics are relatively simple: it is caused by mutations in methyl CPG-binding protein 2 (MeCP2). Our investigation revealed reduced numbers of synapses and dendritic spine density (FIGS. 9a-c), as well as altered calcium transients and spontaneous postsynaptic currents, in RTT patient-derived neurons compared to familial controls (Marchetto M C N, Carromeu C, Acab A, Yu D, Yeo G W, Mu Y, et al. A Model for Neural Development and Treatment of Rett Syndrome Using Human Induced Pluripotent Stem Cells. Cell. 2010; 143(4): 527-39).

Excitingly, we were also able to demonstrate that IGF-1, which reverses some RTT phenotypes in mice, rescued the synapse number defect. However, given the limitations of 2D culture, we were unable to assess either cell volume, which may be altered given RTT patients' microcephaly, or migration. By combining human iPSC technology with 3D biomaterial engineering, we seek to advance the field of human in vitro modeling and generate a novel model of human brain development for to the study of disease.

This system could be relevant to any neurodevelopmental disorder: not only monogenic disorders (e.g., RTT, Angelman, and Timothy syndrome), but also those with more complex inheritance such as other autism spectrum disorders. As the assays may reveal novel deficiencies in NPCs or neurons from patients with any of these disorders, this work enables the creation of several means of screening drugs. Our model should reveal a wider range of differences than apparent in 2D culture and thus should identify more drug leads, providing a powerful screening tool.

In conclusion, we introduce a novel multilayer single step polymerization technique that separates phases by solvent density. This method is accessible, versatile, and facilitates control of discrete, as well as continuously graduated, mechanical and chemical interfaces within structurally uninterrupted hydrogel networks. Although we demonstrated this technique in photopolymerized model hydrogel scaffolds, this simple method can be applied to any polymer system. We apply a sucrose DGMP method to spatially control mechanics, encapsulated proteins, and covalently bound small molecules within hydrogel matrices. We use iodixanol DGMP to pattern bioactive peptides and cells on 2D tissue culture substrates.

Importantly, the range of geometries and feature sizes presented throughout this communication were fabricated with common laboratory equipment and reagents. This powerful and adaptable technique is compatible with a range of polymer types (including those suitable for in vivo applications, such as hyaluronic acid) and solvents, as iodixanol is also compatible with organic solvents. DGMP could be combined with a multitude of current fabrication paradigms to increase the complexity of matrices for tissue engineering, controlled drug delivery, or biological investigation.

Experimental Methods

Cell Maintenance

C2C12 murine myoblasts (AATC) were maintained in Dulbecco's Modified Eagle's Medium supplemented with fetal bovine serum (10% v/v) and penicillin/streptomycin (1% 100× v/v) at 37° C./5% $CO_2$/95% relative humidity. Cell culture reagents were obtained from Life Technologies.

Figure 12:
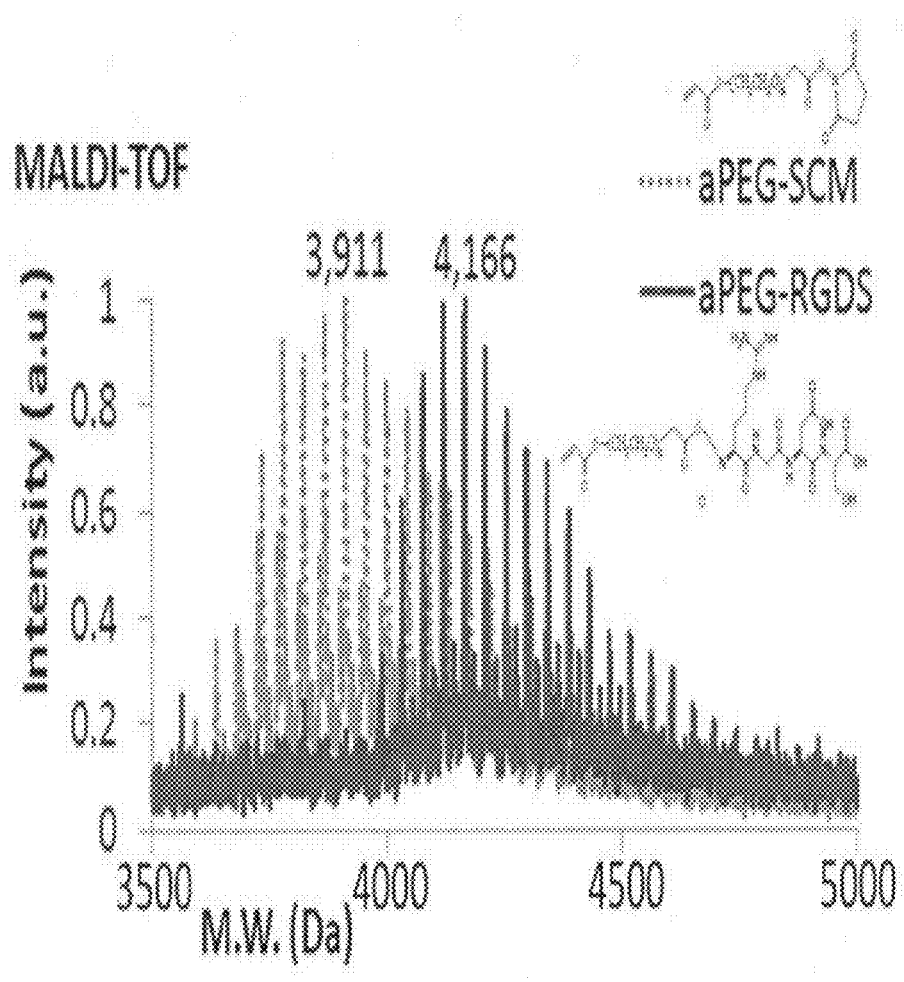
FIG. 12 is a picture of the MALDI-TOF that confirms aPEG-SCM and aPEG-RGDS. Samples dissolved in methanol and drop cast with universal matrix.
Figure 13:
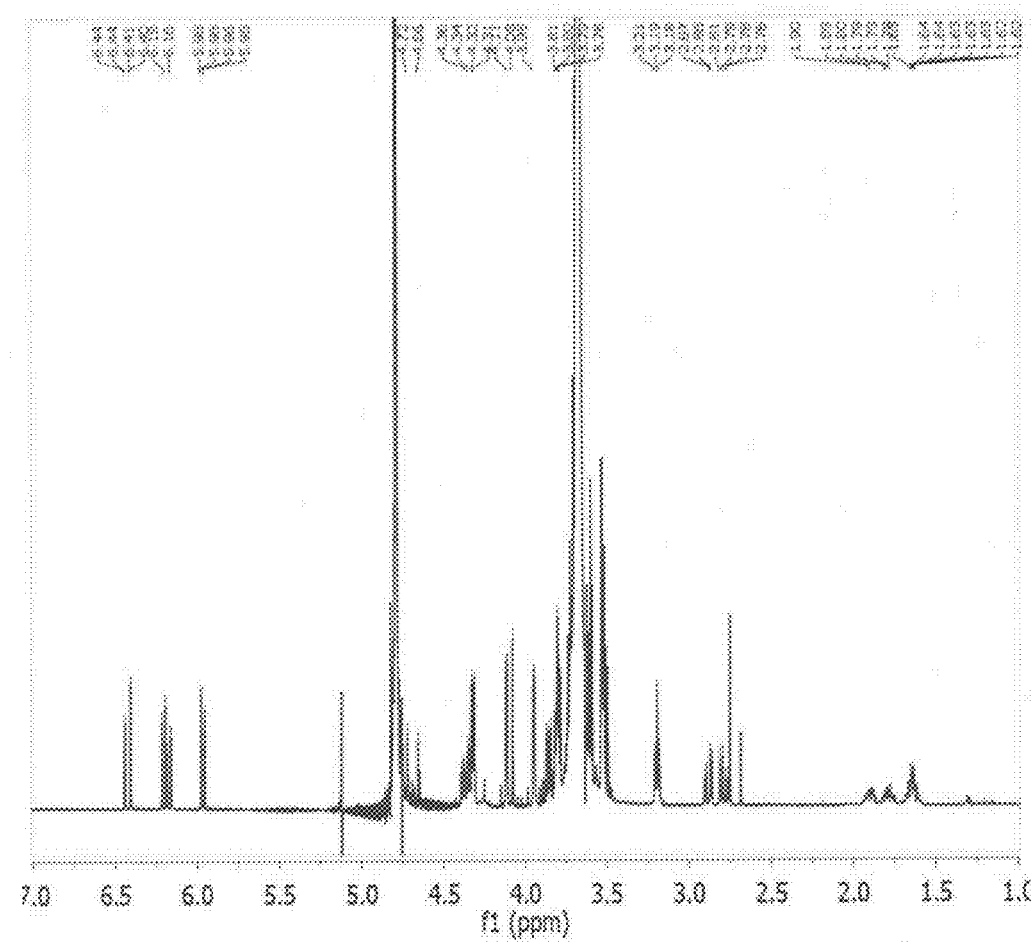
FIG. 13 is a picture of the $^1$H-NMR that confirms acryloyl-PEG-RGDS.

Fluorescently Labeled aPEG-RGDS Synthesis aPEG-RGDS-350 was synthesized with slight modifications to a previously described procedure (J. L. West, J. C. Hoffmann, Soft Matter 2010, 6, 5056). Briefly, RGDS peptide (American Peptide, Arginine-Glycine-Aspartic Acid Serine) was conjugated to PEG (MW 3400 g mol-1) by reaction with aPEG-SCM (Laysan Bio, SCM: Succinimidyl Carboxymethyl) at 1.2:1 molar ratio in the presence of DIPEA at 1.2:2 molar ratio overnight in DMSO under argon at room temperature. aPEG-RGDS was purified by dialysis, lyophilized and confirmed via matrix-assisted laser desorption/ionization time-of-flight mass spectrometry (MALDI-TOF) in universal matrix (Sigma) (FIG. 12) and 1H-NMR in D2O (FIG. 13).

An equimolar amount of Alexa Fluor 350 carboxylic acid, succinimidyl ester (Molecular Probes) was then added to aPEG-RGDS dissolved in DMF overnight in DMSO under argon at room temperature and purified by dialysis, lyophilized and stored under argon at −20° C.

Multilayer Hydrogel Fabrication

For 3D sucrose DGMP (FIG. 1a): aqueous solutions of ethylene glycol diacrylate (Dajac Labs, MW 4000 g mol-1; 10%, 15%, or 20% w/v; FIGS. 2a-b and FIG. 3d) or acrylamide (Promega; 10% w/v; FIGS. 2c-2g) were separately prepared in water. Precursor densities were individually modified with serial concentrations (0-50% w/v) of sucrose.

Each solution was gently layered in transparent cylindrical polypropylene molds made from modified syringes (FIGS. 2a-g) or in hydrophobic silanated (Sigmacote, Sigma) glass Pasteur pipettes (FIG. 3d). For 2D iodixanol DGMP (FIG. 1b): aqueous precursor monomer solutions of ethylene glycol diacrylate (15% w/v, FIG. 3a-c) were separately prepared in Dulbecco's phosphate buffered saline (w/Ca/Mg, HyClone). Precursor densities were modified with serial concentrations (5-40% w/v) of iodixanol (Axis-Shield OptiPrep, 60% iodixanol in water).

Each solution was gently layered in molds made from 0.8 mm thick silicone spacers cut with 10 mm and 8 mm biopsy punches (Acuderm) and sandwiched between hydrophobic silanated glass slides (FIG. 3a). For all precursor solutions, Durocur 2959 photoinitiator (Gibco) was held constant (10 µl mL-1 of 300 mg mL-1 in N-vinyl pyrrolidone). Free radical polymerization was photoinitiated under irradiation with 365 nm light for 1 min in a Luzchem Research UV chamber (~2500 mW cm-2) per side unless otherwise noted. Gradients were agitated in ten volumes of PBS for at least two days with two buffer exchanges per day to remove density modifiers, unreacted prepolymer, and photoinitiator.

Structural Stratification

DGMP gradients were compared to sequentially polymerized multi-layer hydrogels, in which precursors identical to those for DGMP were used, both groups were irradiated for 1 min per layer, and the process was not optimized. For microstructural examination (FIGS. 2a-b), bilayer PEGda hydrogels (10% w/v, upper left; 20% w/v, lower right), were snap frozen in N2, lyophilized overnight, and coated with chromium (45 s at 130 mA), then recorded with an FEI XL30 SFEG SEM. For macrostructural examination and mechanical testing (FIGS. 2c-f), five-layer PAM (10% w/v, 1% w/w crosslink) hydrogels were photographed (FIGS. 2c-d) and compressed with a Satec materials testing machine (FIGS. 2e-f).

To examine the effect of graduated transitions on structural properties, PAM mechanical gradients were created in biphasic sucrose gradients by diffusion of bisacrylamide from layers of 7% to 1% (w/w) crosslinker for $t_S$ of 0, 15, 30, 60, 120, and 180 min (FIG. 2g).

Chemical Stratification

For fluorescence pattern images of PEGda tissue culture discs (FIGS. 3a and 3c), co-dissolved iodixanol and prepolymer solutions were combined with either methacryloxyethyl thiocarbamoyl rhodamine B (Polysciences, 20 µM) or aPEG-RGDS-350 (8 mM). Precursor solutions were gently layered stepwise into silicone and glass molds, described above, and photopolymerized.

Bioactivity of patterned integrin-binding peptide, RGDS, was evaluated by seeding C2C12 myoblasts (20,000 cells cm-2) onto hydrogel discs. Resulting cell patterns were observed after 24 hrs in culture via epifluorescence and phase-contrast imaging (Zeiss Axiovert 200; FIG. 2c). Protein gradients in PEGda (15% w/v) were created via biphasic sucrose DGMP by counter-diffusion of OVA-488 (FIG. 3d, upper) and BSA-594 (FIG. 3d, lower) for $t_S$ of 0, 30, 90, and 150 min (both proteins initially 4 mg ml-1, Life Technologies).

Photography and Image Processing

Gross hydrogel images were obtained in a BioRad Versa-Doc-4000MP. Color photographs were taken with a Canon Powershot A11000 IS. Individual field fluorescence and transmitted light microscopy images were color composited with Image Pro Plus software. All multi-field images were manually reconstructed with ImageJ software (NIH) using the MosaicJ plugin with all corrections disabled (e.g. blending, smart color, and rotation). Average and line fluorescence intensity profiles were generated with Image J software.

Listed below are several advantages, demonstrated in this study, of the density gradient multilayer polymerization (DGMP) method. DGMP is more versatile and accessible compared to complex alternative methods. Moreover, DGMP allows fast, simple fabrication of structurally uninterrupted complex tissue scaffolds with spatially controlled bioactive chemical and mechanical cues.

- Robust: Structurally uninterrupted interfaces, even for unmatched mechanics.
- Facile & Economical: Single polymerization step & commonly available, inexpensive reagents.
- Tunable: Geometry, matrix porosity, and extra-matrix constituents.
- Scalable: Amenable to complementary methods to further control micro- and nano-architectures & vascularity.

Synthesis of Fluorescently Labeled Acryloyl-PEG-RGDS

1. React the RGDS peptide with acryloyl-PEG-succinimidyl carboxymethyl ester (aPEG-SCM, PEG MW: 3400 g/mol) and N-Ndiisopropylethylamine (DIPEA) at 1.2:1:2 molar ratios in dimethyl sulfoxide (DMSO) under argon at room temperature overnight.
2. Confirm conjugation by matrix-assisted laser desorption/ionization time of flight (MALDI-TOF) mass spectrometry. Add 1 µl of aPEG-RGDS reaction solution to a sample spot on the MALDI target and dry. Prepare a saturated solution of Universal MALDI Matrix in tetrahydrofuran (THF) and vortex for 1 min. Add ~1 µl of this solution to the same sample spot. Repeat the procedure for aPEG-SCM for comparison. Load and analyze. The molecular weight of aPEG-RGDS should be greater than aPEG-SCM (FIG. 12).
3. To conjugate the fluorophore, add an equimolar amount of Alexa Fluor 350 carboxylic acid (succinimidyl ester), dissolved in a minimal volume of DMSO, to the aPEG-RGDS reaction solution from 1.1 and react under argon at room temperature overnight.
4. Purify aPEG-RGDS-350 by dialyzing (MW 3500 Da) against DI-H2O at 4° C. for 48 hr at 1,000:1 volumetric ratio, exchanging dialysate at least twice per day.
5. Freeze dry the purified aPEG-RGDS-350 in a Labconco Freezone Plus or equivalent freeze dry system and store at −20° C.

Figure 1:
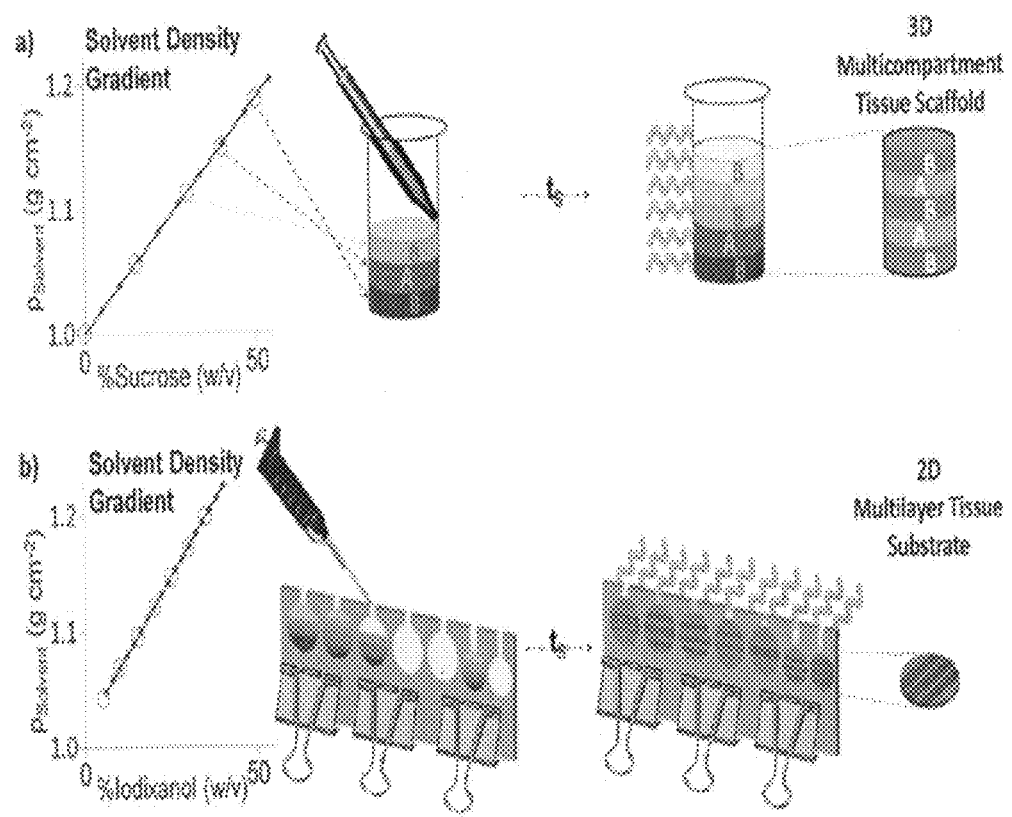
FIG. 1 is a schematic representation of two variations of the Density Gradient Multilayer Polymerization (DGMP) method. (a) Five serially diluted solutions of sucrose co-dissolved with a prepolymer; and either fluorescently-tagged protein A or B. (b) Seven serially diluted solutions of iodixanol co-dissolved with a prepolymer and either methacrylated rhodamine or RGDS-350. Then, after designated settling time (tS), stratified hydrogels are bulk polymerized. The density modifier can be washed away, leaving stable microstructures.

Preparation of a 2D Mold & Fabrication of 2D PEG Gel with Alternating RGDS-350 Layers 1. Prepare hydrophobic glass slides. Place clean glass slides into a glass dish in a vacuum oven. Heat to 80° C. for 30 min to completely dry the surfaces. Place dish with slides in a fume hood and add 250 µl Sigmacote to each slide, gently rocking for 30 sec to coat entire surface. Thoroughly rinse the coated slides with 100% methanol, followed by washing in distilled water, soaking twice for 5 min in at least 10 ml.
2. Cut silicone spacers (0.8 mm thick) with 10 mm biopsy punches.
3. Autoclave the silicone spacers and Sigmacote-treated glass slides.
4. Formulate solutions for each respective layer in individual microfuge tubes by mixing PEG diacrylate (PEGda) precursor (final concentration 15% w/v) with different amounts of iodixanol (60% stock solution in water) to yield varying final concentrations (e.g. 40%, 30%, 20% and 10%), supplementing the remaining volume with phosphate buffered saline (PBS) to obtain solutions of graded densities. In a similar manner, for alternating layers, mix aPEG-RGDS-350 (final concentration 8 mM) with iodixanol and PBS to yield various concentrations (e.g. 35%, 25%, and 15%).
5. Add photoinitiator (2-Hydroxy-4'-(2-hydroxyethoxy)-2-methylpropiophenone, 333 mg/ml stock in N-vinyl pyrrolidone) to each solution for various layers (10 µl of stock solution per ml of each layer solution). Photoinitiator is added last to prevent polymerization before layering of the gels in the mold, as it is sensitive to light.
6. Subsequent steps of are performed in a biosafety cabinet to ensure sterility.
7. Filter-sterilize each solution using a sterile 1 ml syringe and 0.2 µm filter. Assemble the mold setup by sandwiching the spacer between two Sigmacore-treated glass slides and secure with clamps placing as depicted in FIG. 1.
8. Cast the layered gels by adding the most dense solution (e.g. PEGda with 40% iodixanol) first, followed by a less dense solution (e.g. aPEGRGDS-350 with 35% iodixanol). Repeat the alternate layering to achieve several layers of desired composition and densities as shown in FIG. 1.
9. Irradiate the mold with 365 nm light for 3 min using a portable UVR-9000 lamp. Allow the polymerized gels to cure for 5 min. Remove the clamps, then gently lift the top glass slide and the mold; the stratified DGMP gels remain on the slides. Using a sterile spatula, carefully place the gels in a 50 ml tube containing sterile PBS or culture medium for washing.
10. Wash the polymerized gels in PBS at 1,000:1 volumetric ratio, exchanging buffer at least twice per day to remove the density modifier, photoinitiator, and unreacted polymer. Alternatively, PBS may be exchanged with cell growth medium. Store the DGMP gels in PBS or growth medium for the cell culture experiment outlined in Step 3.
11. To visualize alternating layers, arrange DGMP gel (these gels are not suitable for cell culture) along a ruler on the sample tray of a VersaDoc gel documentation unit. Expose the gels in 350 nm; the exposure time varies depending on the concentration of the fluorophore.

2D Cell Culture on DGMP Gels

1. For gels incorporating RGDS peptide, use adhesion dependent cells, such as C2C12 myoblasts.
2. Gently insert DGMP gels (stored in PBS) into the wells of 48-well cell culture plates using a sterile cell scraper in a biosafety cabinet.
3. Pre-warm growth medium (Dulbecco's modified Eagle's medium or DMEM supplemented with 10% v/v fetal bovine serum and 1% v/v 100× penicillin-streptomycin solution) and PBS in a water bath set at 37° C.
4. Wash a 60% confluent plate (10 mm) of C2C12 cells three times with PBS. Aspirate off PBS and harvest cells by adding 1 ml of 0.25% Trypsin-EDTA and incubating at 37° C. for 2 min. Resuspend the cells in growth medium and count cells. Seed the DGMP gel-containing cell culture well with C2C12 myoblasts (20,000 cells/cm2). Incubate the cells at 37° C. in 5% CO2/95% relative humidity. Gently exchange medium after 4 hr, careful not to remove lightly adhered cells.
5. After 24 hr, the attachment of C2C12 myoblasts on the RGDS-containing layers of DGMP gels may be confirmed by epifluorescence and phase contrast microscopy (Zeiss Axiovert 200).

Complex, Cell-Laden, Multilayer Hyerogel Matrices

The DGMP method, a breakthrough for its simplicity in creating complex, cell-laden, multilayer hydrogel matrices. Layering, polymerization (by UV exposure if using radically polymerized materials), and initial iodixanol washout all take approximately 25 minutes.

Hyaluronan-Based Hydrogel Matrices

Figure 10:
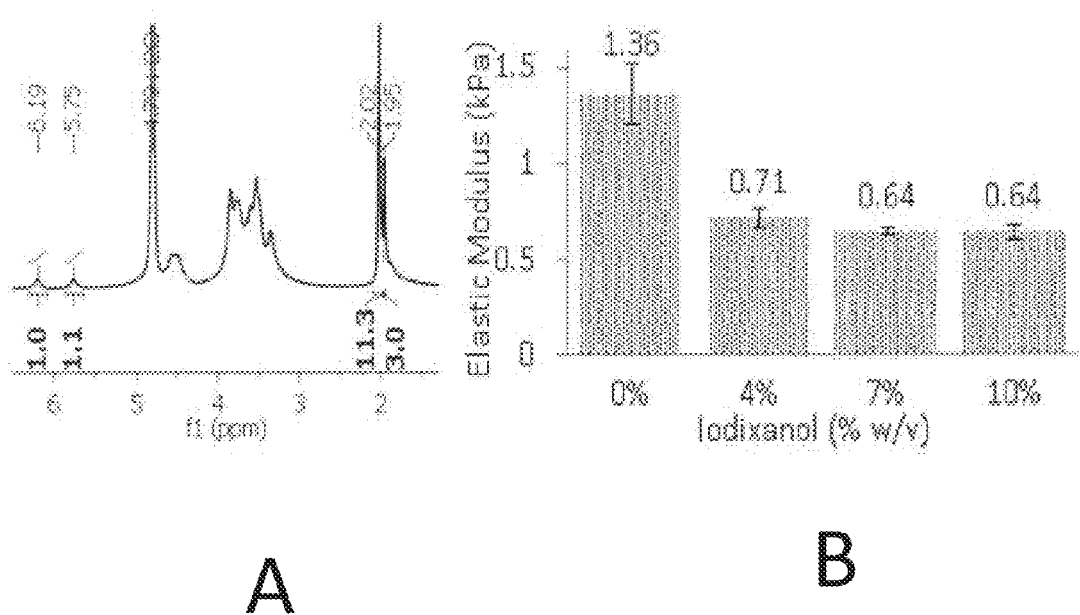
FIG. 10 illustrated the production of hyaluronic acid methacrylate (HMMA) appropriate for NPC culture. (a) NMR characterizations of modified hyaluronic acid with 0.27 methacrylates per disaccharide repeat (HAMA-DS0.27). (b) Elastic moduli of HAMA-DS0.27 (1% w/v) matrices with varied concentrations of iodixanol density modifier characterized by AFM.

Hyaluronic acid methacrylate (HAMA) was synthesized using the method described in Seidlits S K, et al, The effects of hyaluronic acid hydrogels with tunable mechanical properties on neural progenitor cell differentiation. Biomaterials. 2010; 31(14):3930-40, with appropriate resulting elastic modulus for neuron culture (FIG. 10) (Smeds K A, et al., Synthesis of a Novel Polysaccharide Hydrogel, Journal of Macromolecular Science, Part A. 1999; 36(7-8):981-9).

As iodixanol may affect matrix elastic modulus, atomic force microscopy (AFM) was performed. Initial results suggest that its effect is concentration independent in the range under investigation (FIG. 10b). It was also observed that iodixanol minimally affects viability; groups were compared by the ratio of constitutively expressed EGFP to ethidium homodimer-1 staining.

NPCs generated from human iPSCs following informed consent (under protocols approved by the UCSD Institutional Review Board and the Embryonic Stem Cell Research Oversight Committee), generated by transduction of Sox2, Oct4, c-Myc and Klf4. NPCs are produced by dissociating neural rosettes and confirmed by immunocytochemistry against early neural progenitor markers, such as nestin (FIG. 11c) (Marchetto M C N, et al. A Model for Neural Development and Treatment of Rett Syndrome Using Human Induced Pluripotent Stem Cells. Cell. 2010; 143(4):527-39). NPCs are labeled by infection with a lentivirus carrying the CAG promoter driven EGFP reporter (CAG::EGFP).

Figure 11:
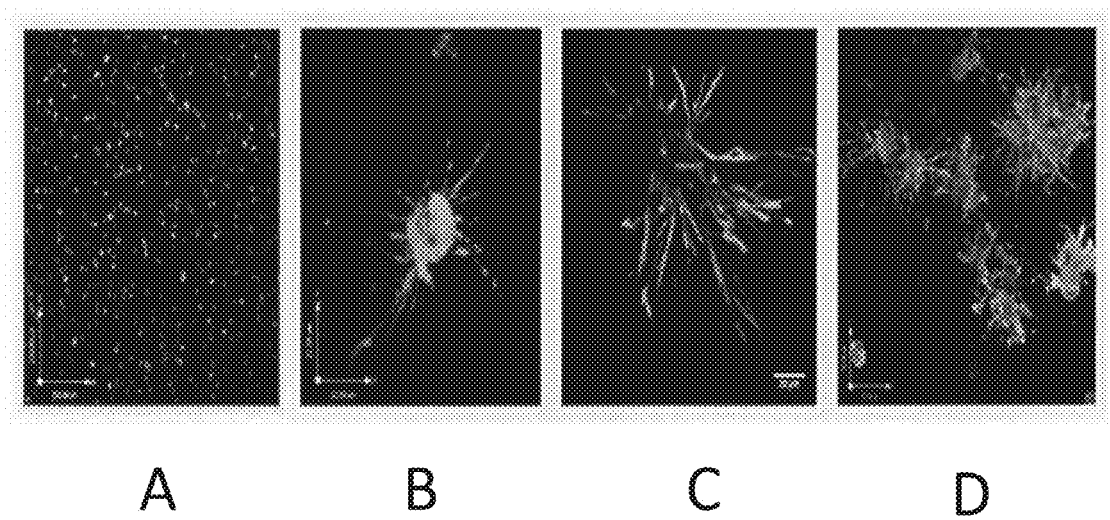
FIG. 11 shown the encapsulation in HAMA is compatible with NPC neurite extension and neuronal differentiation. (a) Viability assay of encapsulated iPSC-derived NPCs (cmv:: EGFP) in 3D HAMA matrices, day 1. "Live" EGFP expression (green) and "dead" nuclear staining (red for 1.4 million cells/mL in HAMA photopolymerized with a combination of acrylated YIGSR-NH2 (250 µM) and RGDS (250 µM). Scale bar, 250 µm. (b) Combination of YIGSR-NH2 (250 µM) and RGDS (250 µM) permits neurite growth from an aggregate of NPCs. Scale bar, 22 µm. (c) NPC maintenance evidenced by expression of nestin when cultured with FGF at day 12 post encapsulation, counterstained with DAPI. Scalebar 20 µm. (d) Neurogenesis evidenced by expression of MAP2 (magenta) at day 10 pose encapsulation, in the presence of BDNF for 1 week, counterstained of F-actin and EGFP. Scalebar 33 µm.

Combinations of tethered adhesion peptides and varied encapsulated cell densities are investigated to improve viability and promote neurite extension. A combination of YIGSR, a peptide sequence of laminin responsible for integrin binding, and RGDS, a peptide that binds many integrins, yields the highest 24 hr viability (~80%, FIG. 11a). This combination also promotes extensive neurite growth by NPCs (FIG. 11b). Not only do HAMA matrices maintain NPCs (nestin expression, FIG. 11c), they also support differentiation when soluble BDNF is provided in the media (MAP2 expression, FIG. 11d).

Development of a 3D Scaffold to Maintain NPC Viability

Cell, adhesion peptide, and photoinitiator concentration, as well as HAMA degree of substitution (DS), are adjusted to establish consistent NPC viability. To maintain NPC multipotency, cells are cultured in an NPC medium with FGF2, barring differentiation and limiting neurite outgrowth. Percent EGFP positive cells is assessed via FACS analysis. HAMA with varied DS, which affects elastic modulus, is synthesized by adjusting molar ratios of reactants, methacrylic acid, and hyaluronan (Smeds K A, et al., Synthesis of a Novel pOlysaccharide Hydrogel, Journal of Macromolecular Science, Part A. 1999; 36(7-8):981-9).

Since scaffold elastic modulus affect differentiation (Seidlits S K, et al. The effects of hyaluronic acid hydrogels with tunable mechanical properties on neural progenitor cell differentiation. Biomaterials. 2010; 31(14):3930-40) and pore size affects locomotion, hydrogel elastic modulus and pore size are measured for each condition tested. Viability is assessed as in preliminary experiments (FIG. 11A).

Outcomes: A set of permissive (later referred to as "baseline") conditions that reliably promote cell viability (at least 90% of total encapsulated cells) with little effect on cell spreading, migration, and neurite outgrowth are identified. It is then determined which adhesion cues are required to prevent anoikis and, through fine tuning, what range of crosslinking density allows nutrient transport, cell locomotion, and neurite outgrowth.

Alternative Approaches: If necessary, encapsulation conditions are modified to balance photoinitiator concentration with UVA exposure time, or add cytoprotective elements such as human serum albumins to enhance encapsulated cell viability. The viability assay we are proposing may be difficult to interpret at late time points due to optically inseparable cell aggregates (FIGS. 10b-d); viability analysis by a DNA-normalized metabolic assay (MTS), or by FACS analysis of dissociated cells following enzymatic digestion can also be considered. Further, if 800 μm thick hydrogels (chosen for ease of handling) are too thick to allow nutrient and oxygen diffusion, thinner constructs are fabricated.

Determination of Variables that Modulate NPC Migration

Many variables influence NPC migration, so focus is applied to those inherent to the matrix itself. The gradients of crosslink densities or concentrations of extracellular matrix derived integrin-binding peptides YIGSR, IKVAV, and RGD, both individually and in combination, are examined. Non-gradient hydrogel matrices serve as controls.

Figure 14:
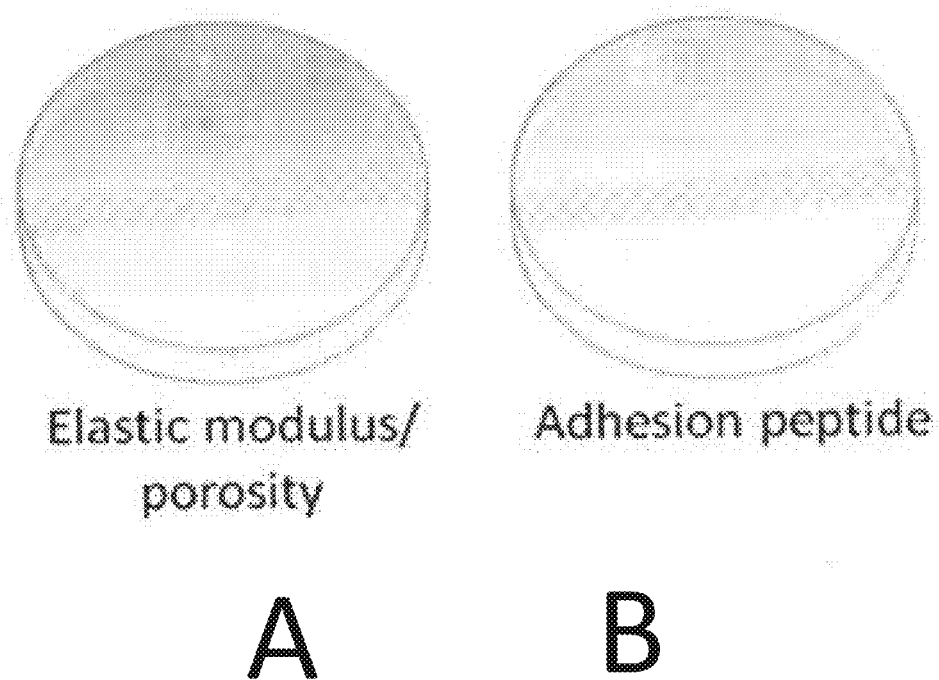
FIG. 14 illustrates a determination of NPC migration variables. NPCs are seeded in the middle layer. (a) Elastic modulus/porosity. (b) Adhesion Peptide.

While many cues that promote directional migration of cell bodies may also promote neurite extension in the same direction, cultures are maintained in NPC medium (with FGF2) to limit outgrowth. In each of these experiments, cells are encapsulated in the middle layer of a HAMA matrix in which adjacent layers contain semi-continuous gradients (FIG. 14). The cell-loaded layer is fluorescently marked with methacrylated rhodamine-B and match the conditions determined to maintain NPC viability.

Figure 15:
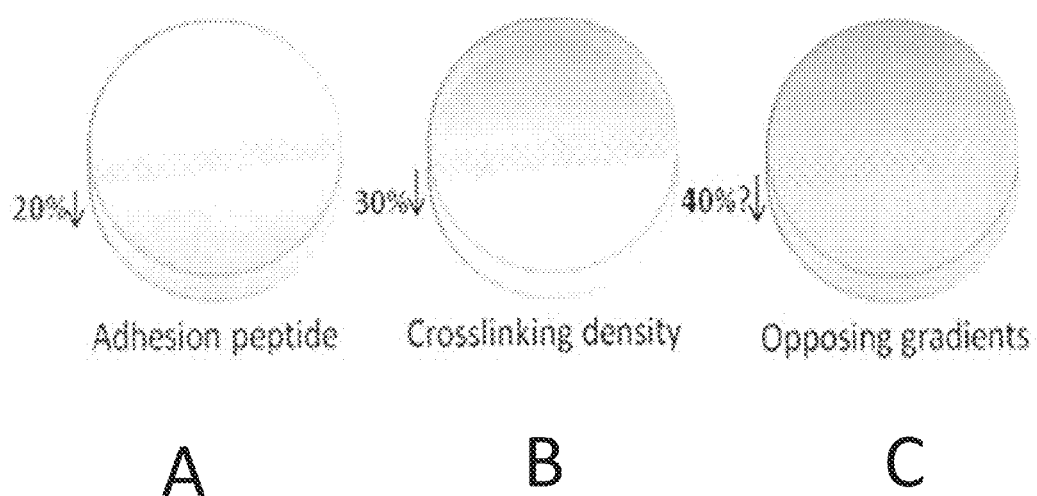
FIG. 15 illustrates the combination of variables to allow NPC migration. Percentages indicated hypothetical migration. This combination may allow grated migration than that in either gradient alone. (a) Adhesion Peptide. (b) Crosslinking Density. (c) Opposing Gradients.

Migration is quantified using confocal microscopy at static time points and, when feasible, with time-lapse imaging. NPCs are monitored daily to determine preferential migration up or down gradients of each variable or combination of variables. The total number of cells crossing into adjacent layers and total distance traveled away from the initial center layer are measured. The combinations of gradients or opposing gradients are further measured to enhance migration (FIG. 15).

Outcomes: A gradient conditions that reliably facilitate cell migration is identified. Contrary to many somatic cell types, NPCs are expected to migrate towards decreasing crosslinking density (HAMA DS), as migration in HAMA has been demonstrated to coincide with hydrogel degradation (Seidlits S K, Khaing Z Z, Petersen R R, Nickels J D, Vanscoy J E, Shear J B, et al. The effects of hyaluronic acid hydrogels with tunable mechanical properties on neural progenitor cell differentiation. Biomaterials. 2010; 31(14):3930-40). We expect NPCs to migrate towards greater concentrations of adhesion peptide (Tate M C, Garcia A J, Keselowsky B G, Schumm M A, Archer D R, LaPlaca M C. Specific 131 integrins mediate adhesion, migration, and differentiation of neural progenitors derived from the embryonic striatum. Molecular and Cellular Neuroscience. 2004; 27(1):22-31; Luo Y, Shoichet M S. A photolabile hydrogel for guided three-dimensional cell growth and migration. Nat Mater. 2004; 3(4):249-53).

Alternative approaches: If spontaneous migration does not occur, the scaffolds are co-cultured with underlying 2D cultures of astrocytes, which have been shown to promote neural migration (Mason H A, Ito S, Corfas G. Extracellular Signals That Regulate the Tangential Migration of Olfactory Bulb Neuronal Precursors: Inducers, Inhibitors, and Repellents. The Journal of Neuroscience. 2001; 21(19):7654-63).

Alternately, by tethering to the HAMA macromer (Yu X, Dillon G P, Bellamkonda R B. A laminin and nerve growth factor-laden three-dimensional scaffold for enhanced neurite extension. Tissue Eng. 1999; 5(4):291-304), gradients of proteins that direct NPC migration may be in corporated, e.g. sonic hedgehog (SHH) (Wylie R G, Ahsan S, Aizawa Y, Maxwell K L, Morshead C M, Shoichet M S. Spatially controlled simultaneous patterning of multiple growth factors in three-dimensional hydrogels. Nat Mater. 2011; 10(10):799-806).

If necessary, an additional level of control over combination gradients is employed: the DGMP method can be combined with a gradient grayscale mask method to independently adjust peptide and elastic modulus gradients by exposing DGMP layered prepolymers to variable amounts of UVA (Tse J R, Engler A J. Preparation of Hydrogel Substrates with Tunable Mechanical Properties. Current Protocols in Cell Biology: John Wiley & Sons, Inc.; 2001).

Creation of Organized 3D Neural Networks

Gradient variables that enhance neurite outgrowth from neurons are identified and, by incorporating a non-adjacent synaptic target cell layer, a model in which cell bodies, axons, and synapses may be easily located and separately analyzed is developed.

This organization simplified a wide array of investigations, such as quantification of synapses and analyses of 3D morphology, e.g. axon packing and alignment. Further, a 3D environment is likely more representative of neural behavior in vivo. In order to generate 3D neuronal networks, NPCs are induced to differentiate by switching to medium without FGF2.

In order to direct oriented neurite outgrowth, gel-inherent variables are considered, and a range of HAMA DS as well as adhesion peptide concentrations are examined. If a gradient of a particular variable, for example IKVAV peptide, directs both neurite outgrowth and cell migration, hydrogel mechanical properties are tailored to fall outside an expected range of migration-permissive elasticity (Hynes S R, Rauch M F, Bertram J P, Lavik E B. A library of tunable poly(ethylene glycol)/poly(L-lysine) hydrogels to investigate the material cues that influence neural stem cell differentiation. Journal of Biomedical Materials Research Part A. 2009; 89A(2):499-509).

Neurite outgrowth from EGFP-expressing neurons is monitored daily by confocal microscopy, and, when effective conditions are identified, by time-lapse imaging. To identify the variable, or combination of variables, that best promotes neurite extension, the total number and length of neurites extending out of the baseline layer in experimental matrices are compared to those in control, non-gradient matrices.

Figure 16:
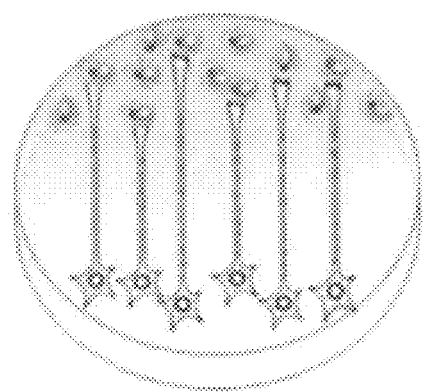
FIG. 16 illustrates the separation of cell bodies from synapses. Neurons synapse onto HEK cells encapsulate din a non-adjacent layer.
Figure 17:
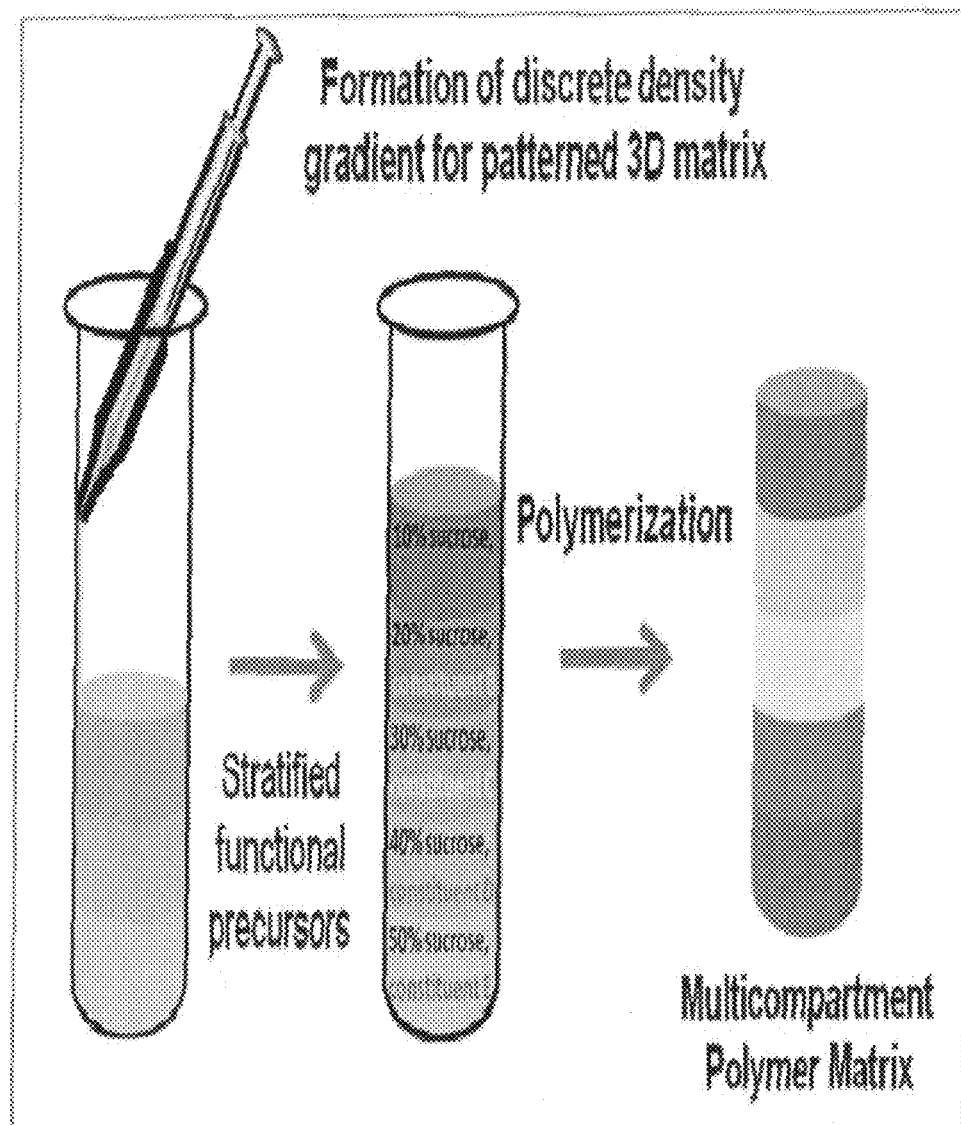
FIG. 17 is a schematic of the adaptable DGMP method to pattern discrete or continuous features (A-E) within an uninterrupted hydrogel matrix in a single polymerization step.
Figure 18:
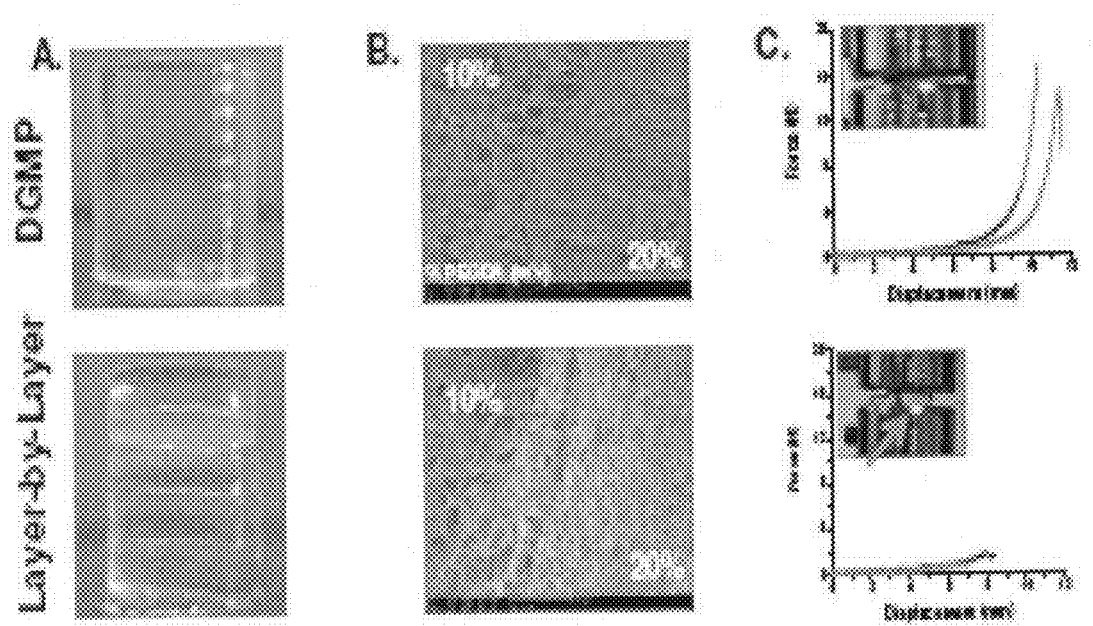
FIG. 18 is a comparison of photoinitiated DGMP to sequential polymerization. (A) Five-layer PEGDA hydrogels (B) Boundaries of bi-layer PEGDA; FE-SEM (C) Multilayer hydrogel ultimate tensile strength and compressive failure mode.
Figure 19:
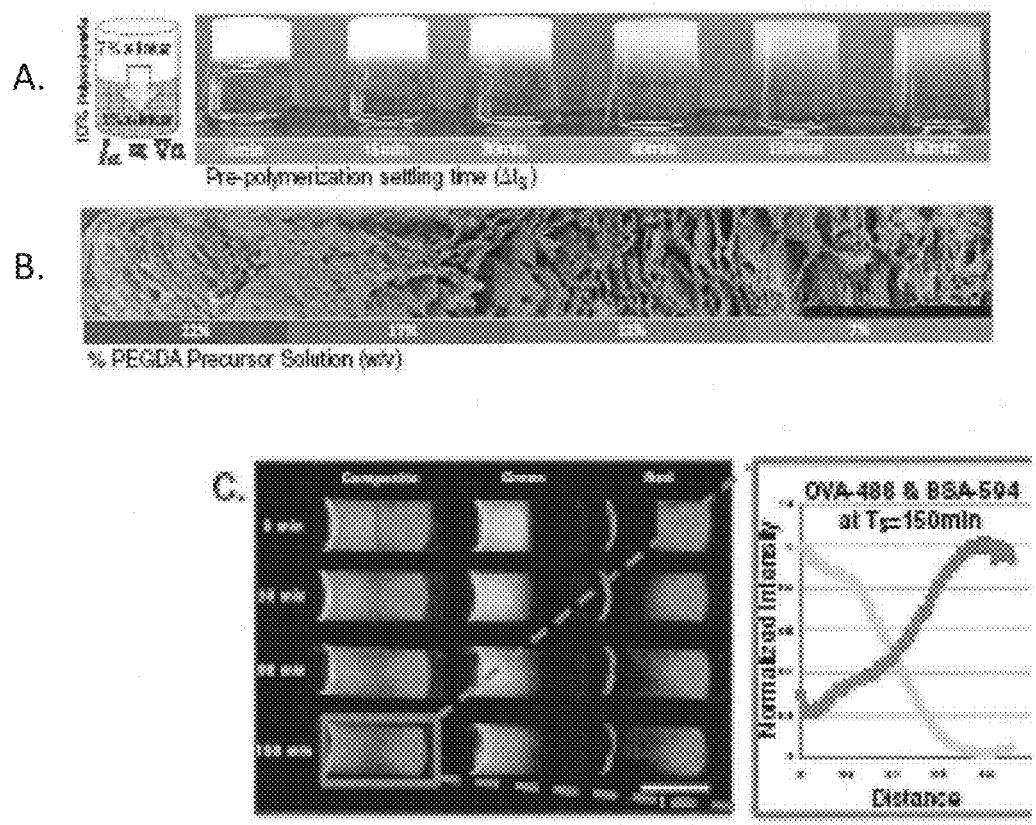
FIG. 19 is a demonstration of tunable process variables. (A) Adjacent compartment swelling is modulated by equilibrating crosslinker gradients for polyacrylamide/Bisacrylamide. (B) Adjacent compartment porosity is modulated by DGMP of varied PEGDA concentration. (C) Encapsulated protein gradients are modulated by using two opposing equilibrating model proteins.
Figure 20:
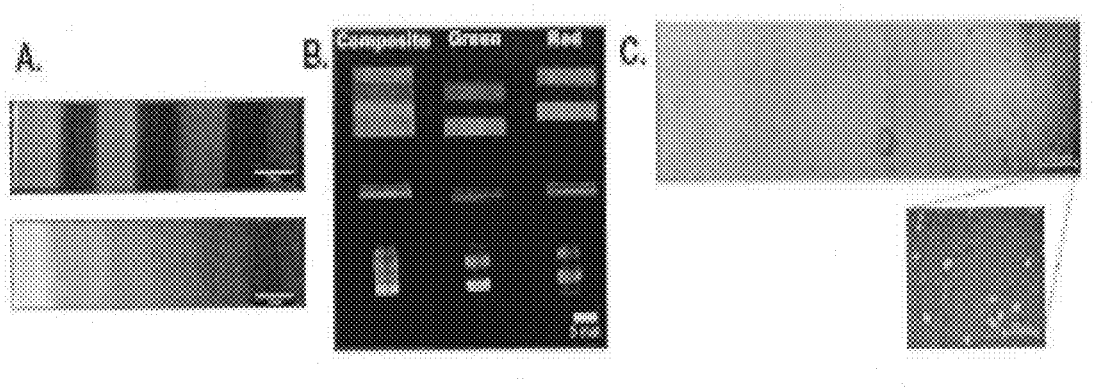
FIG. 20 is an illustration of the biologically relevant adaptability. (A) PEGDA hydrogels with encapsulated BSA-594 in alternate or adjacent stepwise dilutions. (B) Various geometries of polyacrylamide hydrogels with alternately incorporated fluorescein & rhodamine B for visualization. (C) Five-layer PEG hydrogel substrates with A-PEG-RGDS incorporated into alternating layers via DGMP promotes patterned adhesion of HeLa:CMV-GFP cells.

A model in which somatic target cells is used to enable the distinction between pre- and postsynaptic cells is developed. Initially, examples of previous mixed-culture systems are followed for the study of synapses, which often employ HEK293 cells heterologously expressing at least one postsynaptic protein, e.g. neuroligin-1 (Kim J-E, O'Sullivan M L, Sanchez C A, Hwang M, Israel M A, Brennand K, et al. Investigating synapse formation and function using human pluripotent stem cell-derived neurons. Proceedings of the National Academy of Sciences. 2011; 108(7):3005-10). Target HEK293 cells are encapsulated within a non-adjacent layer separated from neurons by a neurite-promoting gradient (FIG. 16).

A range of encapsulation cell densities are analyzed to determine which yields the most efficient synaptogenesis. The co-culture system allows for the distinction between self synapses from synapses onto target cells, which will only express one postsynaptic protein. Synapses are quantified by comparing the number of sites of staining for presynaptic markers (synapsin) to those for postsynaptic markers expressed in neurons and not target cells (PSD95).

Outcomes: A set of variables that promotes neurite outgrowth (of length similar to that observed in 2D cultures) while simultaneously inhibiting migration out of the baseline layer in which cells are encapsulated are identified. Adhesion peptides are expected to be effective in directing neurite extension, as gradients of peptides have previously been demonstrated to drive differential outgrowth in hydrogel matrices in 3D (Sundararaghavan H G, Masand S N, Shreiber D I. Microfluidic generation of haptotactic gradients through 3D collagen gels for enhanced neurite growth. Journal of neurotrauma. 2011; 28(11):2377-87. PMCID: 3218382).

Alternative approaches: A particular degree of difference in biochemical or mechanical variables across layers (i.e., gradient steepness) may selectively promote neurite outgrowth over migration; therefore, varying degrees of difference in HAMA DS or adhesion peptide concentration may be investigated. If no combination of structural and adhesion peptide gradients promotes directional neurite outgrowth, gradients of tethered protein axonal guidance cues are explored.

Further, if mature neurons fail to extend sufficiently long neurites, medium is supplemented with instructional soluble growth factors such as BDNF, which enhances differentiation (FIG. 11d) (Labelle C, Leclerc N. Exogenous BDNF, NT-3 and NT-4 differentially regulate neurite outgrowth in cultured hippocampal neurons. Developmental Brain Research. 2000; 123(1):1-11).

If few neurites form synapses, the transfection approach is modified to enhance expression of postsynaptic protein by incorporating more copies of the gene or by using a more active promoter. Alternatively, an alternate target cell type, such as COST, or a different postsynaptic protein, such as synCAM-1 may be employed.

Comparison of RTT-Derived NPCs and Neurons to Controls

The spatially controlled 3D model of neurodevelopment should be useful to compare NPCs and neurons of distinct genotypes, therefore applicable to answer questions regarding RTT, such as evaluating the effects of either 3D culture microenvironment or scaffold mechanical properties on function and differentiation of human induced pluripotent stem cell derived neuronal progenitor cells into neurons.

NPC Migration

The microcephaly often observed in RTT patients and the connection between abnormal neural stem cell migration and autism (Penagarikano O, et al., Absence of CNTNAP2 Leads to Epilepsy, Neuronal Migration Abnormalities, and Core Autism-Related Deficits. Cell. 2011; 147(1):235-46) suggest that NPC migration may be altered in RTT. Migration of RTT and control NPCs is evaluatted in the migration-promoting conditions discussed above.

To examine NPC migration, RTT and control NPCs (both expressing EGFP) are encapsulated in the 3D hydrogels in parallel under FGF2 conditions to promote NPC maintenance. RTT or control NPCs are encapsulated in a hydrogel layer adjacent to a layer containing a gradient promoting unidirectional NPC migration, using the parameters determined earlier. NPC migration is then quantified via live confocal microscopy with time-lapse imaging and at static time points.

Alternative strategies: Detection of differences between RTT and controls in the NPC migration assays may not be visable if adhesion peptides presented do not allow for the demonstration of impaired migration, as RTT neurons may not have defective laminin binding. Alternatively, adhesion cues shown to be affected in RTT can be used.

Neurite Outgrowth and Synaptogenesis

Given our previous results of decreased synapse number and spine density in RTT neurons, we seek to further explore related phenotypes such as neurite extension and dendritic arborization. Dynamic neurite outgrowth in patient-derived RTT neurons has not yet been examined, so these experiments will yield novel results. As 3D environments enhance connectivity, a more pronounced defect in synaptogenesis is expected.

RTT and control NPCs are induced to differentiate after encapsulation in 3D hydrogel scaffolds constructed using the parameters identified above. To measure neurite outgrowth, cells are immunostained with a neuronal marker (Map2) or transduced with a synapsin::EGFP reporter and imaged via confocal microscopy (with time-lapse imaging as needed). To quantify synapses, target cells (e.g. HEK) expressing a postsynaptic protein are encapsulated in the layer opposite that promoting unidirectional neurite outgrowth. Synapses onto target cells are quantified by confocal microscopy, using antibodies against the presynaptic proteins synapsin and neurexin and two postsynaptic proteins: that expressed by target cells, and one expressed in neurons, e.g. PSD95.

Alternative strategies: If no significant differences between RTT and controls in the neurite outgrowth assays are detected, the guidance cues presented may not allow for the demonstration of impaired neurite outgrowth. In that case, guidance cues suggested to be involved in RTT are incorporated instead.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

Although this application has been described in detail above, it will be understood by one of ordinary skill in the art that various modifications can be made without departing from the spirit of the invention. Accordingly, this application is limited only by the following claims.

What is claimed:

1. A method for preparing a multicompartment hydrogel comprising:
    a. co-dissolving a polymer precursor with an inert density modifier in multiple solvent fractions to a create prepolymer solutions with different densities;
    b. layering the prepolymer solutions on top of each other in an order proceeding from high to low solvent density; and
    c. irradiating the prepolymer solutions to form a polymer.

2. The method of claim 1, wherein the polymer precursor comprises acrylamide and bisacrylamide.

3. The method of claim 1, wherein the polymer precursor comprises polyethylene glycol diacrylate (PEGda).

4. The method of claim 1, wherein co-dissolving further comprises adding an acrylated fluorophore or a conjugated RGD-containing adhesion peptide to the prepolymer solutions.

5. The method of claim 1, wherein one or more of the layers of the prepolymer solutions are irradiated at different times.

6. The method of claim 1, wherein the inert density modifier comprises sucrose, iodixanol, or a mixture thereof.

7. The method of claim 1, wherein the inert density modifier is present in an amount of between about 0% to about 15% or between about 10% to about 50%.

8. The method of claim 1, further comprising washing out the inert density modifier after the polymer is formed.

9. The method of claim 1, wherein the multicompartment hydrogel is configured for culturing tissue in a three-dimensional arrangement.

10. The method of claim 1, wherein co-dissolving comprises serially diluting the polymer precursor with the inert density modifier to progressively create the prepolymer solutions in order of decreasing densities.

11. A method for creating a multicompartment polymer matrix, comprising:
    creating a plurality of prepolymer solutions of decreasing densities by serially co-dissolving an inert density modifier with a prepolymer;
    progressively layering the plurality of prepolymer solutions in a mold in order of decreasing density, wherein density differences between adjacent layers induce phase separations between layers; and
    exposing the layered prepolymer solutions to a polymerizing radiation source to form a polymer.

12. The method of claim 11, wherein the step of creating further comprises co-dissolving one or more of cells, ligands, proteins and peptides.

13. The method of claim 11, wherein the prepolymer comprises acrylamide and bisacrylamide.

14. The method of claim 11, wherein the prepolymer comprises polyethylene glycol diacrylate (PEGda).

15. The method of claim 11, wherein co-dissolving further comprises adding an acrylated fluorophore or a conjugated RGD-containing adhesion peptide.

16. The method of claim 11, further comprising washing the polymer to remove the inert density modifier.

17. The method of claim 11, wherein the inert density modifier comprises sucrose, iodixanol, or a mixture thereof.

18. A method for creating a multicompartment polymer matrix, comprising:
    creating a plurality of prepolymer solutions of decreasing densities by serially co-dissolving an inert density modifier with a prepolymer;
    layering the plurality of prepolymer solutions in a mold in layers progressing from higher to lower density solutions, wherein density differences between adjacent layers induce phase separations between layers; and exposing the layered prepolymer solutions to a polymerizing radiation source to form a polymer.

19. The method of claim 18, wherein the layering is repeated to produce layered combinations of higher to lower density layers.

20. The method of claim 18, wherein the step of creating further comprises co-dissolving one or more of cells, ligands, proteins and peptides with the prepolymer and the inert density modifier.

* * * * *